(12) United States Patent
Lake et al.

(10) Patent No.: US 8,946,186 B2
(45) Date of Patent: Feb. 3, 2015

(54) QSOX1 AS AN ANTI-NEOPLASTIC DRUG TARGET

(71) Applicant: Arizona Board of Regents, a body corporate of the State of Arizona, acting for and on behalf of Arizona State, Scottsdale, AZ (US)

(72) Inventors: Douglas Lake, Scottsdale, AZ (US); Benjamin Katchman, Tempe, AZ (US)

(73) Assignee: Arizona Board of Regents, a Body Corporate of the State of Arizona Acting for and on Behalf of Arizona State University, Scottsdale, AR (US)

( * ) Notice: Subject to any disclaimer, the term of this patent is extended or adjusted under 35 U.S.C. 154(b) by 0 days.

(21) Appl. No.: 13/847,930

(22) Filed: Mar. 20, 2013

(65) Prior Publication Data
US 2013/0287793 A1    Oct. 31, 2013

Related U.S. Application Data

(63) Continuation-in-part of application No. PCT/US2011/052122, filed on Sep. 19, 2011.

(60) Provisional application No. 61/722,396, filed on Nov. 5, 2012, provisional application No. 61/384,502, filed on Sep. 20, 2010.

(51) Int. Cl.
*C12N 15/11*   (2006.01)
*C12Q 1/68*    (2006.01)
*C12N 15/113*  (2010.01)

(52) U.S. Cl.
CPC ..... *C12N 15/1137* (2013.01); *C12Y 108/03002* (2013.01)
USPC ........................................ 514/44 A; 435/6.1

(58) Field of Classification Search
CPC ................... C12N 2310/14; C12N 2310/531; C12N 15/1135; C12N 15/111; C12Y 108/03002; A61K 38/44
See application file for complete search history.

(56) References Cited

U.S. PATENT DOCUMENTS

| | | | |
|---|---|---|---|
| 6,664,057 B2 | 12/2003 | Albertson et al. | |
| 8,357,667 B2 | 1/2013 | Korc | |
| 8,551,971 B2 | 10/2013 | Furukawa | |
| 2005/0255487 A1* | 11/2005 | Khvorova et al. | 435/6 |
| 2013/0078279 A1 | 3/2013 | Nemunaitis et al. | |

FOREIGN PATENT DOCUMENTS

| | | |
|---|---|---|
| WO | 2010/071787 A1 | 6/2010 |
| WO | 2010/071788 A1 | 6/2010 |
| WO | 2010/077921 A1 | 7/2010 |
| WO | 2010/086384 A1 | 8/2010 |

OTHER PUBLICATIONS

Alon, Assaf, et al., "QSOX contains a pseudo-dimer of functional and degenerate sulfhydryl oxidase domains," FEBS Lett., Apr. 2010, pp. 1521-1525, vol. 584, No. 8.

Alon, Assaf, et al., "The dynamic disulphide relay of quiescin sulphydryl oxidase," Nature, Aug. 2012, pp. 414-418, vol. 488, No. 7411.

American Cancer Society, "Cancer Facts and Figures 2012," Atlanta: American Cancer Society, 2012, pp. 1-68.

Antwi, Kwasi, et al., "Analysis of the plasma peptidome from pancreas cancer patients connects a peptide in plasma to overexpression of the parent protein in tumors," J. Proteome Res., Oct. 2009, pp. 4722-4731, vol. 8, No. 10.

Bacac, Marina, et al, "Metastatic Cancer Cell," Annu. Rev. Pathol., 2008, pp. 221-247, vol. 3.

Bardeesy Nabeel, et al., "Pancreatic cancer biology and genetics," Nat. Rev. Cancer, Dec. 2002, pp. 897-909, vol. 2, No. 12.

Bauvois, Brigitte, "New facets of matrix metalloproteinases MMP-2 and MMP-9 as cell surface transducers: Outside-in signaling and relationship to tumor progression," Biochim. Biophys. Acta, Jan. 2012, pp. 29-36, vol. 1825, No. 1.

Blick, T. et al., "Epithelial mesenchymal transition traits in human breast cancer cell lines," Clin. Exp. Metastasis, May 2008, pp. 629-642, vol. 26, No. 6.

Bloomston, Mark, et al., "Matrix metalloproteinases and their role in pancreatic cancer: a review of preclinical studies and clinical trials," Ann. Surg. Oncol., Aug. 2002, pp. 668-674, vol. 9, No. 7.

Bowen, Cai, et al., "Loss of NKX3.1 expression in human prostate cancers correlates with tumor progression," Cancer Res., Nov. 2000, pp. 6111-6115, vol. 60, No. 21.

Caffarel, Maria M., et al., "Cannabinoids reduce ErbB2-driven breast cancer progression through Akt inhibition," Mol. Cancer, Jul. 2010, p. 196, vol. 9.

Chen, Yongqiang, et al., "The regulation of autophagy-unanswered questions," J. Cell Sci., Jan. 2010, pp. 161-170, vol. 124, Pt. 2.

Coppock, Donald L., et al., "The quiescin Q6 gene (QSCN6) is a fusion of two ancient gene families: thioredoxin and ERV1," Genomics, Dec. 1998, pp. 460-468, vol. 54, No. 3.

Coppock, Donald L., et al., "Regulation of the Quiescence-Induced Genes: Quiescin Q6, Decorin, and Ribosomal Protein S29," Biochem. Biophys. Res. Commun., Mar. 2000, pp. 604-610, vol. 269, No. 2.

Coppock, Donald L., et al., "Multidomain flavin-dependent sulfhydryl oxidases," Antioxid. Redox. Signal, Mar. 2006, pp. 300-311, vol. 8, Nos. 3-4.

Coppock, Donald L., et al., "Preferential gene expression in quiescent human lung fibroblasts," Cell Growth Differ., Jun. 1993, pp. 483-493, vol. 4, No. 6.

(Continued)

*Primary Examiner* — Tracy Vivlemore
*Assistant Examiner* — Kate Poliakova-Georgantas
(74) *Attorney, Agent, or Firm* — McDonnell Boehnen Hulbert & Berhoff LLP

(57) ABSTRACT

The present invention provides methods for tumor treatment by administering an inhibitor of quiescin sulfhydryl oxidase 1 (QSOX1), compositions comprising such inhibitors, and methods for identifying such inhibitors.

28 Claims, 11 Drawing Sheets

(56) References Cited

OTHER PUBLICATIONS

De Andrade, Claudia R., et al., "Quiescin sulfhydryl oxidase (QSOX) is expressed in the human atheroma core: possible role in apoptosis," In Vitro Cell Dev. Biol. Anim., Dec. 2011, pp. 716-727, vol. 47, No. 10.
Deer, Emily L, et al., "Phenotype and Genotype of Pancreatic Cancer Cell Lines," Pancreas, May 2010, pp. 425-435, vol. 39, No. 4.
Evan, Gerard I., et al., "Proliferation, cell cycle and apoptosis in cancer," Nature, May 2001, pp. 342-348, vol. 411, No. 6835.
Fass, Deborah, "The Erv family of sulfhydryl oxidases," Biochim. Biophys. Acta, Apr. 2008, pp. 557-566, vol. 1783, No. 4.
Hanahan, Douglas, et al., "Hallmarks of cancer: the next generation," Cell, Mar. 2011, pp. 646-674, vol. 144, No. 5.
Heckler, Erin J., et al., "Human Quiescin-Sulfhydryl Oxidase, QSOX1: Probing Internal Redox Steps by Mutagenesis." Biochem., Apr. 2008, pp. 4955-4963, vol. 47, No. 17.
Heckler, Erin J., et al., "Generating disulfides with the Quiescin-sulfhydryl oxidases," Biochim. Biophys. Acta, Apr. 2008, pp. 567-577, vol. 1783, No. 4.
Hellebrekers, Debby M.E.I.,et al., "Identification of Epigenetically Silenced Genes in Tumor Endothelial Cells", Cancer Res., May 2007, pp. 4138-4148, vol. 67, No. 9.
Hoober, Karen L., et al., "Flavin-dependent sulfhydryl oxidases in protein disulfide bond formation" Methods Enzymol., 2002, pp. 30-34, vol. 348.
Hoober, Karen L, et al., "A sulfhydryl oxidase from chicken egg white," J. Biol. Chem., Nov. 1996, pp. 30510-30519, vol. 271, No. 48.
Hoober, Karen L, et al., "Homology between egg white sulfhydryl oxidase and quiescin Q6 defines a new class of flavin linked sulfhydryl oxidases," J. Biol. Chem., Nov. 1999, pp. 31759-31762, vol. 274, No. 45.
Hu, Min, et al., "Molecular characterization of the tumor microenvironment in breast cancer," Eur. J. Cancer, Dec. 2008, pp. 2760-2765, vol. 44, No. 18.
Jin, Quanri, et al., "Fatty acid synthase phosphorylation: a novel therapeutic target in HER2-overexpressing breast cancer cells," Breast Cancer Res., 2010, p. R96, vol. 12, No. 6.
Katchman, Benjamin A., et al., "Quiescin Sulfhydryl Oxidase 1 Promotes Invasion of Pancreatic Tumor Cells Mediated by Matrix Metalloproteinases," Mol. Cancer Res., Dec. 2011, pp. 1621-1631, vol. 9, No. 12.
Kessenbrock, Kai, et al., "Matrix metalloproteinases: regulators of the tumor microenvironment," Cell, Apr. 2010, pp. 52-67, vol. 141, No. 1.
Khoo, Boon Yin, et al., "Modification of MCF-10A Cells with Pioglitazone and Serum-Rich Growth Medium Increases Soluble Factors in the Conditioned Medium, Likely Reducing BT-474 Cell Growth," Int. J. Mol. Sci., 2012, pp. 5607-5627, vol. 13.
Kohrmann, Andrea, et al., "Expression of matrix metalloproteinases (MMPs) in primary human breast cancer and breast cancer cell lines: New findings and review of the literature," BMC Cancer, Jun. 2009, p. 188, vol. 9.
Koorstra, Jan-Bart, et al., "Morphogenesis of pancreatic cancer: role of pancreatic intraepithelial neoplasia (PanINs)," Langenbecks Arch. Surg., Jul. 2008, pp. 561-570, vol. 393, No. 4.
Koshiba, Takatomo, et al., "Involvement of matrix metalloproteinase-2 activity in invasion and metastasis of pancreatic carcinoma," Cancer, Feb. 1998, pp. 642-650, vol. 82, No. 4.
Kupai, K., et al. "Matrix metalloproteinase activity assays: Importance of zymography," J. Pharmacol. Toxicol. Methods, Mar-Apr. 2010, pp. 205-209, vol. 61, No. 2.
Lambert, Paul A., et al., "Antiproliferative and antiinvasive effects of carboxyamido-triazole on breast cancer cell lines," Surgery, Aug. 1997, pp. 372-379, vol. 122, No. 2.
Martin, Katherine J., et al., "Prognostic Breast Cancer Signature Identified from 3D Culture Model Accurately Predicts Clinical Outcome across Independent Datasets," PLoS ONE, Aug. 2008, p. e2994, vol. 3, No. 8.
Michor, Franziska, et al., "The Origins and Implications of Intratumor Heterogeneity," Cancer Prev. Res. (Phila), Nov. 2010, pp. 1361-1364, vol. 3, No. 11.
Morel, Carole, et al., "Involvement of sulfhydryl oxidase QSOX1 in the protection of cells against oxidative stress-induced apoptosis," Exp. Cell Res., Nov. 2007, pp. 3971-3982, vol. 313, No. 19.
Ouyang, Xuesong, et al., "Loss-of-function of Nkx3.1 promotes increased oxidative damage in prostate carcinogenesis," Cancer Res., Aug. 2005, pp. 6773-6779, vol. 65, No. 15.
Ouyang, Xuesong, et al., "Immortal human pancreatic duct epithelial cell lines with near normal genotype and phenotype," Am. J. Pathol., Nov. 2000, pp. 1623-1631, vol. 157, No. 5.
Plati, Jessica, et al., "Apoptotic cell signaling in cancer progression and therapy," Integr. Biol. (Camb.), Apr. 2011, pp. 279-296, vol. 3, No. 4.
Polyak, Kornelia, "Heterogeneity in breast cancer," J. Clin. Invest., Oct. 2011, pp. 3786-3788, vol. 121, No. 10.
Pryczynicz, Anna, et al., "Expression of matrix metalloproteinase 9 in pancreatic ductal carcinoma is associated with tumor metastasis formation," Folia Histochem. Cytobiol., 2007, pp. 37-40, vol. 45, No. 1.
Radisky, Evette S., et al., "Matrix Metalloproteinase-Induced Epithelial-Mesenchymal Transition in Breast Cancer," J. Mammary Gland Biol. Neoplasia, Jun. 2010, pp. 201-212, vol. 15, No. 2.
Ringner, Markus, et al., "GOBO: Gene Expression-Based Outcome for Breast Cancer Online," PLoS ONE, Mar. 2011, p. e17911, vol. 6, No. 3.
Rizki, Aylin, et al., "A Human Breast Cell Model of Preinvasive to Invasive Transition," Cancer Res., Mar. 2008, pp. 1378-1387, vol. 68, No. 5.
Schoning, K.-U., et al., "Chemical etiology of nucleic acid structure: the alpha-threofluransyl (3' to 2') oligonucleotide system" Science, Nov. 17, 2000, pp. 1347-1351, vol. 290, No. 5495.
Sgroi, Dennis C., "Preinvasive Breast Cancer," Annu. Rev. Pathol., 2010, pp. 193-221, vol. 5.
Siegel, Rebecca, et al., "Cancer statistics, 2012," CA. Cancer J. Clin., Jan.-Feb. 2012, pp. 10-29, vol. 62, No. 1.
Snoek-Van Beurden, Patricia A.M., et al., "Zymographic techniques for the analysis of matrix metalloproteinases and their inhibitors," Biotechniques, Jan. 2005, pp. 73-83, vol. 38, No. 1.
Song, Haengseok, et al., "Loss of Nkx3.1 leads to the activation of discrete downstream target genes during prostate tumorigenesis," Oncogene, Sep. 2009, pp. 3307-3319, vol. 28, No. 37.
Sorlie, Therese, et al., "Gene expression patterns of breast carcinomas distinguish tumor subclasses with clinical implications," Proc. Natl. Acad. Sci. USA, Sep. 2001, pp. 10869-10874, vol. 98, No. 19.
Strauss-Soukup, J.K., et al., "Effects of neutralization pattern and stereochemistry on DNA bending by methyiphosphonate substitutions," Biochemistry, Jul. 1997, pp. 8692-8698, vol. 36, No. 29.
Strimpakos, Alexios, et al., "Pancreatic cancer: from molecular pathogenesis to targeted therapy," Cancer Metastasis Rev., Sep. 2008, pp. 495-522, vol. 27, No. 3.
Thorpe, Colin, et al., "Sulfhydryl oxidases: emerging catalysts of protein disulfide bond formation in Eukaryotes," Arch Biochem. Biophys., Sep. 2002, pp. 1-12, vol. 405, No. 1.
Tian, Mei, et al., "Proteomic analysis identifies MMP-9, DJ-1 and A1BG as overexpressed proteins in pancreatic juice from pancreatic ductal adenocarcinoma patients," BMC Cancer, Aug. 2008, p. 241, vol. 8 (11 pages).
Vitu, Elvira, et al., "Gain of function in an ERV/ALR sulfhydryl oxidase by molecular engineering of the shuttle disulfide," J. Mol. Biol., Sep. 2006, pp. 89-101, vol. 362, No. 1.
Wu, Wen-Sheng, "The signaling mechanism of ROS in tumor progression," Cancer Metastasis Rev., Dec. 2006, pp. 695-705, vol. 25, No. 4.
Zuo, Dongmei, et al., "PlasmID: a centralized repository for plasmid clone information and distribution," Nucleic Acids Res., Jan. 2007, p. D680-D684, vol. 35, Database issue.
International Search Report and Written Opinion for PCT/US2011/052122, mailed Nov. 29, 2011 (24 pages).
International Preliminary Report on Patentability for PCT/US2011/052122, mailed Apr. 4, 2013 (17 pages).
Geltosky, Jack, "QSOX1 as an anti-neoplastic drug target," AzTE Web Pub, Aug. 2011, Arizona Technology Enterprises, Scottsdale.

* cited by examiner ium sulfhydryl oxidase 1 (QSOX1) expression and/or activity, or a pharmaceutically acceptable salt thereof, to treat the tumor. In one embodiment, the inhibitor of QSOX1 is selected from the group consisting of anti-QSOX1 antibodies, QSOX1-binding aptamers, QSOX1 antisense oligonucleotides,
QSOX1 AS AN ANTI-NEOPLASTIC DRUG TARGET

CROSS REFERENCE

This application claims priority to U.S. Provisional Patent Application Ser. No. 61/722,396 filed Nov. 5, 2012 and to PCT Application Serial No. PCT/US11/52122 filed Sep. 19, 2011, which claims priority to U.S. Provisional Patent Application Ser. No. 61/384,502 filed Sep. 20, 2010. Each application is incorporated by reference herein in its entirety.

BACKGROUND

Pancreatic ductal adenocarcinoma (PDA) is a disease that carries a poor prognosis. It is often detected in stage III resulting in an unresectable tumor at the time of diagnosis. However, even if pancreatic cancer is surgically resected in stage I or II, it may recur at a metastatic site (1, 2). Currently, patients diagnosed with pancreatic ductal adenocarcinoma have less than a 5% chance of surviving past five years (3).

SUMMARY OF THE INVENTION

In a first aspect, the present invention provides methods for tumor treatment, comprising administering to a subject having a tumor an amount effective of an inhibitor of quiescin sulfhydryl oxidase 1 (QSOX1) expression and/or activity, or a pharmaceutically acceptable salt thereof, to treat the tumor. In one embodiment, the inhibitor of QSOX1 is selected from the group consisting of anti-QSOX1 antibodies, QSOX1-binding aptamers, QSOX1 antisense oligonucleotides, QSOX1 siRNA, and QSOX1 shRNA. In another embodiment, the tumor is a tumor that over-expresses QSOX1 compared to control. In a further embodiment, the subject is one from which tumor-derived QSOX1 peptides can be obtained. In a further embodiment, the tumor is a pancreatic tumor, and preferably a pancreatic adenocarcinoma. In a still further embodiment, the method is for limiting tumor metastasis.

In a second aspect, the present invention provides isolated nucleic acids, comprising or consisting of antisense, siRNA, miRNA, and/or shRNA molecules having a nucleic acid sequence that is perfectly complementary at least 10 contiguous nucleotides of QSOX1 as shown in SEQ ID NO: 1 and 2 or RNA equivalents thereof; and/or fragments of the nucleic acid molecule. In a preferred embodiment, the isolated nucleic acids comprising sequences from the group consisting of

```
                                            (SEQ ID NO: 11)
5'-A(T/U)C(T/U)ACA(T/U)GGC(T/U)GACC(T/U)GGAA-3'

(SEQ ID NO: 12)
5'-AGGAAAGAGGG(T/U)GCCG(T/U)(T/U)C(T/U)(T/U)-3', (SEQ ID NO: 13)
5'-GCCAA(T/U)G(T/U)GG(T/U)GAGAAAG(T/U)(T/U)(T/U)-3', (SEQ ID NO: 14)
5'-GCCAAGAAGG(T/U)GAAC(T/U)GGA(T/U)(T/U)-3'.

(SEQ ID NO: 15)
5'-CCGGACAA(T/U)GAAGAAGCC(T/U)(T/U)(T/U)-3'

(SEQ ID NO: 16)
5'-(T/U)C(T/U)AGCCACAACAGGG(T/U)CAA(T/U)-3'

(SEQ ID NO: 17)
5'-ATCTACATGGCTGACCTGGAA-3', (SEQ ID NO: 18)
5'-AGGAAAGAGGGTGCCGTTCTT-3', (SEQ ID NO: 19)
5'-GCCAATGTGGTGAGAAAGTTT-3', (SEQ ID NO: 20)
5'-GCCAAGAAGGTGAACTGGATT-3', (SEQ ID NO: 21)
5'-CCGGACAATGAAGAAGCCTTT-3';

(SEQ ID NO: 22)
5'-TCTAGCCACAACAGGGTCAAT-3';
and (SEQ ID NO: 26)
5'-CCGGGCCAATGTGGTGAGAAAGTTTCTCGAGAAACTTTCTCACCACATTGGCTTTTG-
3'.
```

In one embodiment of this second aspect of the invention, the isolated nucleic acids present in a short hairpin RNA (shRNA). In a further embodiment, the shRNA is of the general formula:

```
                                            (SEQ ID NO: 23)
CCGG-X1-CTCGAGAAACTTTCTCACCACATTGGCTTTTG-3'
``` wherein X1 is a nucleic acid sequence selected from the group consisting of

```
                                            (SEQ ID NO: 11)
5'-A(T/U)C(T/U)ACA(T/U)GGC(T/U)GACC(T/U)GGAA-3'
```

-continued (SEQ ID NO: 12)
5'-AGGAAAGAGGG(T/U)GCCG(T/U)(T/U)C(T/U)(T/U)-3', (SEQ ID NO: 13)
5'-GCCAA(T/U)G(T/U)GG(T/U)GAGAAAG(T/U)(T/U)(T/U)-3', (SEQ ID NO: 14)
5'-GCCAAGAAGG(T/U)GAAC(T/U)GGA(T/U)(T/U)-3'.

(SEQ ID NO: 15)
5'-CCGGACAA(T/U)GAAGAAGCC(T/U)(T/U)(T/U)-3'

(SEQ ID NO: 16)
5'-(T/U)C(T/U)AGCCACAACAGGG(T/U)CAA(T/U)-3'

(SEQ ID NO: 17)
5'-ATCTACATGGCTGACCTGGAA-3', (SEQ ID NO: 18)
5'-AGGAAAGAGGGTGCCGTTCTT-3', (SEQ ID NO: 19)
5'-GCCAATGTGGTGAGAAAGTTT-3', (SEQ ID NO: 20)
5'-GCCAAGAAGGTGAACTGGATT-3', (SEQ ID NO: 21)
5'-CCGGACAATGAAGAAGCCTTT-3';
and (SEQ ID NO: 22)
5'-TCTAGCCACAACAGGGTCAAT-3'.

In a third aspect, the present invention provides recombinant expression vectors comprising the isolated nucleic acid of any embodiment of the second aspect of the invention operatively linked to a promoter.

In a fourth aspect, the present invention provides recombinant host cells comprising the recombinant expression vector of the third aspect of the invention.

In a fifth aspect, the present invention provides pharmaceutical compositions, comprising
(a) the isolated nucleic acid of any embodiment of the second aspect of the invention, the recombinant expression vector of any embodiment of the third aspect of the invention, or the recombinant host cell of any embodiment of the fourth aspect of the invention; and
(b) a pharmaceutically acceptable carrier.

In a sixth aspect, the present invention provides methods for identifying candidate compounds for treating a tumor, comprising
(a) contacting tumor cells capable of expressing QSOX1 with one or more candidate compounds under conditions suitable for expression of QSOX1;
(b) determining a level of QSOX1 expression and/or activity in the tumor cells and comparing to control;
wherein a compound that decreases QSOX1 expression and/or activity in the tumor cells relative to control is a candidate compound for treating a tumor.

In one embodiment, the tumor cells are pancreatic tumor cells, preferably pancreatic adenocarcinoma cells.

DETAILED DESCRIPTION OF THE INVENTION

Figure 1:
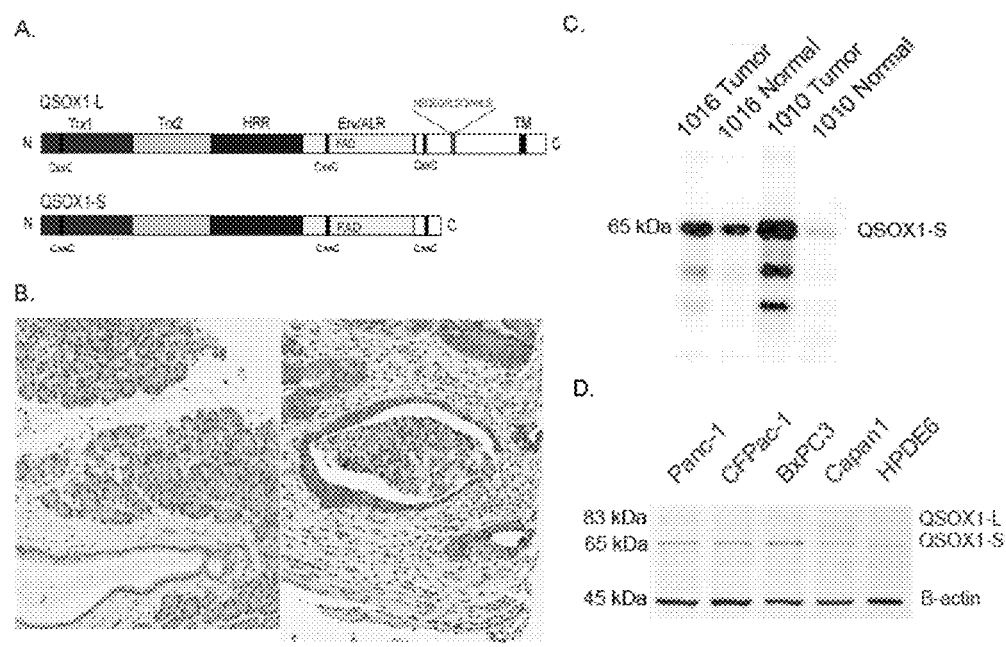
FIG. 1: QSOX1 is highly expressed in tumor cell lines but is not expressed in adjacent normal cells. Previously, our lab discovered a short peptide, NEQEQPLGQWHLS (SEQ ID NO: 3), in patient plasma through LC-MS/MS. We were able to map this short, secreted peptide back to an understudied parent protein, QSOX1-L. A.) Diagram showing the two splice variants of QSOX1, QSOX1-Short (S) and -Long (L), both contains a thioredoxin 1 (Trx1) and ERV/ALR functional domains as well as structural thioredoxin 2 (Trx2) and helix rich region (HRR). QSOX1-L contains a predicted transmembrane (TM) domain. The peptide NEQEQPLGQWHLS (SEQ ID NO: 3), maps back to QSOX1-L, and found to be secreted in pancreatic cancer patients but not in normal samples. The commercially available antibody recognizes the first 329 amino acids of both QSOX1-S and -L. B.) Immunohistochemistry of normal (left) and tumor (right) pancreatic tissue sections that have been stained with the anti-QSOX1 showing tumor specific staining in pancreatic ducts but not in adjacent non-tumor cells. C.) Western blot analysis of patient tumor as well as adjacent normal tissue indicates that QSOX1-S is the dominant splice variant expressed. D.) Western blot showing QSOX1 expression in transformed normal pancreatic cells (HPDE6) and Human Pancreatic Adenocarinoma Cells (Panc-1, CFPac-1, BxPC3, and Capan1) shows that our in vitro system mimics that of the in vivo QSOX1 expression as shown above using IHC.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides methods for tumor treatment, comprising contacting a subject having a tumor with an amount effective of an inhibitor of QSOX1 expression and/or activity, or pharmaceutically acceptable salt thereof, to treat the tumor.

As demonstrated in the examples that follow, the inventors of the present invention have discovered that inhibitors of QSOX1 expression and/or activity of QSOX1 can be used to treat tumors.

As used herein, "QSOX1" is Quiescin Sulfhydryl Oxidase 1, also called QSCN6. The protein accession number for the long variant of QSOX1 on the NCBI database is NP_002817 (SEQ ID NO:24), and the accession number for the short form is NP_001004128 (SEQ ID NO:25). As used herein, "QSOX1" refers to both the long and short variants of QSOX1.

The subject can be any mammal, preferably a human.

As used herein, any suitable "inhibitor of QSOX1 expression and/or activity" can be used that is capable of reducing expression of QSOX1 mRNA expression or protein synthesis, or that can inhibit activity of QSOX1 protein via any mechanism, including but not limited to binding to QSOX1 resulting in inhibition of QSOX1 activity. Such inhibitors can include, but are not limited to small molecules, antibodies, and aptamers that inhibit activity of QSOX1 protein, and antisense, siRNA, shRNA, etc. that inhibit expression of QSOX1 mRNA and/or protein. Inhibitors of QSOX1 expression may be identified through any suitable means, including but not limited to the methods described below. Any suitable method for determining QSOX1 activity levels may be used, including but not limited to those described in detail below.

As used herein, "inhibit" means at least a 10% reduction in QSOX1 expression and/or activity; preferably at least a 20%, 30%, 40%, 50%, 60%, 70%, 80%, 90%, or greater reduction in expression and/or activity.

The methods of the invention can be used to treat any suitable tumor type. In one preferred embodiment, the methods are used to treat any tumor type that over-expresses QSOX1. Expression of QSOX1 can be assessed by any suitable method, including but not limited to immunohistochemistry of suitable tissue sample, polymerase chain reaction, or detection of QSOX1 peptides in suitable tissue, as disclosed, for example, in WO 2010/071788; WO 2010/01787; and WO 2010/077921, incorporated by reference herein in their entirety. In various non-limiting embodiments, techniques that can be used in the analysis include mass spectrometry (MS), two dimensional gel electrophoresis, Western blotting, immunofluorescence, ELISAs, antigen capture assays (including dipstick antigen capture assays) and mass spec immunoassay (MSIA). In one preferred embodiment, ligands for the one or more peptides are used to "capture" antigens out of the tissue sample. Such ligands may include, but are not limited to, antibodies, antibody fragments and aptamers. In one embodiment, the ligand(s) are immobilized on a surface and the sample is passed over the surface under conditions suitable for binding of any peptides in the sample to the ligand(s) immobilized on the surface. Such antigen capture assays permit determining a concentration of the peptides in the tissue sample, as the concentration likely correlates with extent of disease.

The tissue sample may be any suitable sample from which tumor-derived peptides may be obtained. In various preferred embodiments, the tissue sample is selected from the group consisting of plasma, serum, urine, saliva, and relevant tumor tissue. In various preferred embodiments for detecting QSOX1 peptides in tissue (preferably plasma or serum), the peptide to be detected is selected from the group consisting of

NEQEQPLGQWHLS, (SEQ ID NO: 3)

NEQEQPLGQWH, (SEQ ID NO: 4)

EQPLGQWHLS, (SEQ ID NO: 5)

AAPGQEPPEHMAELQR, (SEQ ID NO: 6)

AAPGQEPPEHMAELQ, (SEQ ID NO: 7)

AAPGQEPPEHMAELQRNEQEQPLGQWHLS, (SEQ ID NO: 8)

NEQEQPL, (SEQ ID NO: 9)
and

GQWHLS. (SEQ ID NO: 10)

As used herein, the phrase "an amount effective" refers to the amount of inhibitor that provides a suitable treatment effect.

Any suitable control can be used to compare with QSOX1 expression and/or activity in the subject's tissue. In one embodiment, the control comprises an amount of one or more peptides of interest from a tissue sample from a normal subject or population (ie: known not to be suffering from a tumor), or from a subject or population of subjects suffering from a tumor, using the same detection assay. The control tissue sample will be of the same tissue sample type as that assessed from the test subject. In one preferred embodiment, a standard concentration curve of one or more peptides of interest in the control tissue sample is determined, and the amount of the one or more peptides of interest in the test subject's tissue sample is compared based on the standard curve. In another preferred embodiment for use in monitoring progress of tumor therapy, samples are obtained from patients over time, during or after their therapy, to monitor levels of one or more peptides in plasma as an indication about tumor burden in patients. The control may comprise a time course of concentration of the one or more peptides of interest in a given tissue type of the test subject, to monitor the effect of treatment on the concentration; this embodiment is preferred, for example, when assessing efficacy of tumor treatments. Those of skill in the art will recognize that similar controls can be used for immunohistochemical-based analysis. Based on the teachings herein and the knowledge in the art, those of skill in the art can design a variety of other appropriate controls in assessing QSOX1 expression and/or activity in identifying subjects most likely to respond to the treatment methods of the invention, as well as to assess efficacy of the treatment over time.

Thus, in one preferred embodiment, the method comprises identifying subjects with tumors that over-express QSOX1, and treating such patients according to the methods of the invention. In one preferred embodiment, the method comprises measuring QSOX1 expression in blood plasma to identify tumors that over-express QSOX1. Methods for preparing blood plasma are well known in the art. In one embodiment, plasma is prepared by centrifuging a blood sample under conditions suitable for pelleting of the cellular component of the blood.

Non-limiting tumor types that can be treated using the methods of the invention include pancreatic, lung, colon, breast, and prostate tumors. In a preferred embodiment, the tumor is a pancreatic tumor, such as a pancreatic adenocarcinoma or a neuroendocrine tumor. In a further preferred embodiment, the tumor comprises a pancreatic adenocarcinoma.

As used herein, "treating tumors" means accomplishing one or more of the following: (a) reducing tumor mass; (b) slowing the increase in tumor mass; (c) reducing tumor metastases; (d) slowing the incidence of tumor metastases; (e) limiting or preventing development of symptoms characteristic of cancer; (f) inhibiting worsening of symptoms characteristic of cancer; (g) limiting or preventing recurrence of symptoms characteristic of cancer in subjects that were previously symptomatic; (i) increasing subject survival time; and (j) limiting or reducing morbidity of therapy by enhancing current therapies, permitting decreased dose of current standard of care therapies.

For example, symptoms of pancreatic cancer include, but are not limited to, pain in the upper abdomen, significant weight loss, loss of appetite and/or nausea and vomiting, jaundice, and Trousseau sign. In a preferred embodiment, the methods limit tumor metastasis, such as limiting pancreatic tumor metastasis. As shown in the examples that follow, the inventors have shown that knockdown of QSOX1 expression in tumor cells leads to a dramatic decrease in tumor cell invasive/migratory phenotype, thus making the methods of the invention particularly useful for limiting tumor metastasis. While not being limited by any particular mechanism of action, the inventors believe that this inhibition of metastasis may result from a decrease in the proteolytic activity of matrix metalloproteases 2 and 9 (MMP-2 and MMP-9), as discussed in more detail in the examples that follow.

In a preferred embodiment of all of the above embodiments, the inhibitor is selected from the group consisting of antibodies, antisense RNA, siRNA, miRNA, and shRNA. In a further preferred embodiment, the inhibitor comprises or consists of antisense, siRNA, miRNA, and/or shRNA molecules having a nucleic acid sequence perfectly complementary to least 10 contiguous nucleotides of QSOX1 as shown in SEQ ID NO:1 and 2 or RNA equivalents thereof; and/or fragments of the nucleic acid molecule. In various preferred embodiments, the nucleic acid molecule is perfectly complementary to at least 11, 12, 13, 14, 15, 16, 17, 18, 19, 20, 21, 22, 23, 24, 25 or more contiguous nucleotides of QSOX1, or an RNA equivalent thereof.

In another preferred embodiment, the inhibitor comprises or consists of a nucleic acid selected from the group consisting of (SEQ ID NO: 11)
5'-A(T/U)C(T/U)ACA(T/U)GGC(T/U)GACC(T/U)GGAA-3'

(SEQ ID NO: 12)
5'-AGGAAAGAGGG(T/U)GCCG(T/U)(T/U)C(T/U)(T/U)-3', (SEQ ID NO: 13)
5'-GCCAA(T/U)G(T/U)GG(T/U)GAGAAAG(T/U)(T/U)(T/U)-3', (SEQ ID NO: 14)
5'-GCCAAGAAGG(T/U)GAAC(T/U)GGA(T/U)(T/U)-3', (SEQ ID NO: 15)
5'-CCGGACAA(T/U)GAAGAAGCC(T/U)(T/U)(T/U)-3',
and (SEQ ID NO: 16)
5'-(T/U)C(T/U)AGCCACAACAGGG(T/U)CAA(T/U)-3'.

wherein residues noted as "(T/U)" can be either "T" or "U". In further preferred embodiments, the inhibitor comprises or consists of (SEQ ID NO: 17)
5'-ATCTACATGGCTGACCTGGAA-3', (SEQ ID NO: 18)
5'-AGGAAAGAGGGTGCCGTTCTT-3', (SEQ ID NO: 19)
5'-GCCAATGTGGTGAGAAAGTTT-3', (SEQ ID NO: 20)
5'- GCCAAGAAGGTGAACTGGATT-3', (SEQ ID NO: 21)
5'-CCGGACAATGAAGAAGCCTTT-3';

(SEQ ID NO: 22)
5'-TCTAGCCACAACAGGGTCAAT-3';
and (SEQ ID NO: 26)
5'-CCGGGCCAATGTGGTGAGAAAGTTTCTCGAGAAACTTT CTCACCACATTGGCTTTTTG-3'.

In a further preferred embodiment, the nucleic acids of SEQ ID NO:11-22 are part of a short hairpin RNA (shRNA). In this embodiment, such an shRNA comprises flanking regions, loops, antisense and spacer sequences flanking a recited SEQ ID NO: sequence responsible for the specificity of shRNA. There are no specific sequence requirements for these various other shRNA regions so long as a loop structure can be formed. Exemplary constructs are shown in the examples below. ShRNA are thought to assume a stem-loop structure with a 2 nucleotide 3' overhang that is recognized by Dicer and processed in to siRNA. SiRNA are then recognized by RNA-Induced Silencing Complex (RISC) which removes the sense strand from the stem structure leaving the guide strand allowing it to associate with target mRNA and cleave it: QSOX1, in this case. Full length protein cannot be translated after cleavage.

In one exemplary embodiment, the shRNA comprise or consist of a nucleic acid of the general formula:

(SEQ ID NO: 23)
CCGG-X1-CTCGAGAAACTTTCTCACCACATTGGCTTTTG-3' wherein X1 is a nucleic acid sequence selected from the group consisting of (SEQ ID NO: 11)
5'-A(T/U)C(T/U)ACA(T/U)GGC(T/U)GACC(T/U)GGAA-3'

(SEQ ID NO: 12)
5'-AGGAAAGAGGG(T/U)GCCG(T/U)(T/U)C(T/U)(T/U)-3', (SEQ ID NO: 13)
5'-GCCAA(T/U)G(T/U)GG(T/U)GAGAAAG(T/U)(T/U)(T/U)-3', (SEQ ID NO: 14)
5'-GCCAAGAAGG(T/U)GAAC(T/U)GGA(T/U)(T/U)-3'.

(SEQ ID NO: 15)
5'-CCGGACAA(T/U)GAAGAAGCC(T/U)(T/U)(T/U)-3'

(SEQ ID NO: 16)
5'-(T/U)C(T/U)AGCCACAACAGGG(T/U)CAA(T/U)-3'

(SEQ ID NO: 17)
5'-ATCTACATGGCTGACCTGGAA-3', (SEQ ID NO: 18)
5'-AGGAAAGAGGGTGCCGTTCTT-3', (SEQ ID NO: 19)
5'-GCCAATGTGGTGAGAAAGTTT-3',

-continued

5'-GCCAAGAAGGTGAACTGGATT-3', (SEQ ID NO: 20)

5'-CCGGACAATGAAGAAGCCTTT-3'; (SEQ ID NO: 21)
and

5'-TCTAGCCACAACAGGGTCAAT-3'. (SEQ ID NO: 22)

These and other nucleic acid inhibitors may be modified for a desired purpose, including but not limited to nucleic acid backbone analogues including, but not limited to, phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). Nucleic acid inhibitors may also comprise analogous forms of ribose or deoxyribose as are well known in the art, including but not limited to 2' substituted sugars such as 2'-O-methyl-, 2'-fluoro- or 2'-azido-ribose, carbocyclic sugar analogs, α.-anomeric sugars, epimeric sugars such as arabinose, xyloses or lyxoses, pyranose sugars, sedoheptuloses, acyclic analogs and abasic nucleoside analogs such as methyl riboside. The oligonucleotides may also contain TNA (threose nucleic acid; also referred to as alpha-threofuranosyl oligonucleotides) (See, for example, Schong et al., Science 2000 Nov. 17, 290 (5495):1347-1351.)

The inhibitors for use in the present invention can be administered via any suitable technique or formulation, including but not limited to lipid, virus, polymer, or any other physical, chemical or biological agent, but are generally administered as part of a pharmaceutical composition together with a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.). The isolated nucleic acids or shRNAs can be present in a vector, such as a viral vector (ex: retrovirus, lentivirus, adenovirus, adeno-associated virus, etc.), for delivery via any suitable technique.

These compositions can be prepared in a manner well known in the pharmaceutical art, and can be administered by a variety of routes, depending upon whether local or systemic treatment is desired and upon the area to be treated. Administration may be via physical injection with a needle to, for example, a tumor in the subject; topical (including ophthalmic and to mucous membranes including intranasal, vaginal and rectal delivery); pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more inhibitors described herein above in combination with one or more pharmaceutically acceptable carriers, and may further comprise one or more additional active agents as appropriate for a given therapeutic treatment. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 1 to about 1000 mg, more usually about 10 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. It will be understood, however, that the amount of the compound actually administered will usually be determined by a physician, according to the relevant circumstances, including the condition to be treated, the chosen route of administration, the actual inhibitor administered, the age, weight, and response of the individual patient, the severity of the patient's symptoms, and the like.

The inhibitors described herein can also be formulated in combination with one or more additional active ingredients as desired.

The present invention also provides methods for limiting tumor metastasis, comprising contacting a subject having a tumor with an amount effective of an inhibitor of QSOX1 expression and/or activity, or pharmaceutically acceptable salt thereof, to limit metastasis of the tumor in the subject. As shown in the examples that follow and as discussed above, QSOX1 inhibitors slow tumor growth and inhibit the metastatic process.

All embodiments of the first aspect of the invention are equally applicable to this second aspect, unless the context clearly dictates otherwise. As used herein, "limiting metastasis" means any limitation over what would be seen in the absence of administration of the QSOX1 inhibitor. In a preferred embodiment, limiting metastasis comprises a statistically significant limitation compared to control subjects not treated with the QSOX1 inhibitor. In another preferred embodiment, the tumor comprises a pancreatic tumor; even more preferably a pancreatic adenocarcinoma.

In a second aspect, the present invention provides isolated nucleic acids, comprising or consisting of antisense, siRNA, miRNA, and/or shRNA molecules having a nucleic acid sequence perfectly complementary to least 10 contiguous nucleotides of QSOX1 as shown in SEQ ID NO:1 and 2 or RNA equivalents thereof; and/or fragments of the nucleic acid molecule. In various preferred embodiments, the nucleic acid molecule is perfectly complementary to at least 11, 12, 13, 14, 15, 16, 17, 18, 19, 20, 21, 22, 23, 24, 25 or more contiguous nucleotides of QSOX1, or an RNA equivalent thereof.

In a further preferred embodiment, the isolated nucleic acids comprise or consist of a nucleotide sequence selected from the group consisting of

```
                                          (SEQ ID NO: 11)
5'-A(T/U)C(T/U)ACA(T/U)GGC(T/U)GACC(T/U)GGAA-3'

(SEQ ID NO: 12)
5'-AGGAAAGAGGG(T/U)GCCG(T/U)(T/U)C(T/U)(T/U)-3', (SEQ IDNO: 13)
5'-GCCAA(T/U)G(T/U)GG(T/U)GAGAAAG(T/U)(T/U)(T/U)-
3', (SEQ ID NO: 14)
5'-GCCAAGAAGG(T/U)GAAC(T/U)GGA(T/U)(T/U)-3'.

(SEQ ID NO: 15)
5'-CCGGACAA(T/U)GAAGAAGCC(T/U)(T/U)(T/U)-3'

(SEQ ID NO: 16)
5'-(T/U)C(T/U)AGCCACAACAGGG(T/U)CAA(T/U)-3'

(SEQ ID NO: 17)
5'-ATCTACATGGCTGACCTGGAA-3', (SEQ ID NO: 18)
5'-AGGAAAGAGGGTGCCGTTCTT-3', (SEQ ID NO: 19)
5'-GCCAATGTGGTGAGAAAGTTT-3', (SEQ ID NO: 20)
5'-GCCAAGAAGGTGAACTGGATT-3', (SEQ ID NO: 21)
5'-CCGGACAATGAAGAAGCCTTT-3';

(SEQ ID NO: 22)
5'-TCTAGCCACAACAGGGTCAAT-3';
and (SEQ ID NO: 26)
5'-CCGGGCCAATGTGGTGAGAAAGTTTCTCGAGAAACTTT

CTCACCACATTGGCTTTTTG-3'.
```

The isolated nucleic acids can be used, for example, in the methods of the invention. The isolated nucleic acids of this second aspect of the present invention can be modified as described above in the first aspect of the invention, including nucleic acid backbone analogues and analogous forms of ribose or deoxyribose.

As used herein, "isolated" means that the nucleic acids are removed from their normal surrounding nucleic acid sequences in the genome or in cDNA sequences, and are substantially free of contaminating material used to isolate them (ie: agarose, polyacrylamide, column chromatography resins, and the like). The isolated nucleic acids may be stored in any suitable state, including but not limited to in solution or as a lyophilized powder.

The isolated nucleic acids may be chemically synthesized using means known in the art, or may be generated by recombinant expression vectors.

As used herein, the isolated nucleic acids "comprising" the recited nucleotide sequences means that the recited nucleotide sequences can be present as part of a larger synthetic construct, such as an antisense nucleic acid, siRNA, an shRNA, miRNA, or as part of a construct in association (covalently bound or non-covalently bound) with a lipid, virus, polymer, or any other physical, chemical or biological agent. As used herein, the isolated nucleic acids "comprising" the recited nucleotide sequences does not include the isolated nucleic acid as part of a naturally occurring or isolated full length QSOX1 transcript or cDNA thereof.

In one embodiment, the isolated nucleic acid is present in a short hairpin RNA (shRNA). As discussed above, such an shRNA comprises flanking regions, loops, antisense and spacer sequences flanking a recited SEQ ID NO: sequence responsible for the specificity of shRNA. There are no specific sequence requirements for these various other shRNA regions so long as a loop structure can be formed. Exemplary constructs are shown in the examples below. In one embodiment, the shRNA is of the general formula:

```
                                          (SEQ ID NO: 23)
CCGG-X1-CTCGAGAAACTTTCTCACCACATTGGCTTTTTG-3'
``` wherein X1 is a nucleic acid sequence selected from the group consisting of

```
                                          (SEQ ID NO: 11)
5'-A(T/U)C(T/U)ACA(T/U)GGC(T/U)GACC(T/U)GGAA-3'

(SEQ ID NO:12)
5'-AGGAAAGAGGG(T/U)GCCG(T/U)(T/U)C(T/U)(T/U)-3', (SEQ ID NO: 13)
5'-GCCAA(T/U)G(T/U)GG(T/U)GAGAAAG(T/U)(T/U)(T/U)-
3', (SEQ ID NO: 14)
5'-GCCAAGAAGG(T/U)GAAC(T/U)GGA(T/U)(T/U)-3'.

(SEQ ID NO: 15)
5'-CCGGACAA(T/U)GAAGAAGCC(T/U)(T/U)(T/U)-3'

(SEQ ID NO: 16)
5'-(T/U)C(T/U)AGCCACAACAGGG(T/U)CAA(T/U)-3'

(SEQ ID NO: 17)
5'-ATCTACATGGCTGACCTGGAA-3', (SEQ ID NO: 18)
5'-AGGAAAGAGGGTGCCGTTCTT-3', (SEQ ID NO: 19)
5'-GCCAATGTGGTGAGAAAGTTT-3',
```

-continued

5'-GCCAAGAAGGTGAACTGGATT-3', (SEQ ID NO: 20)

5'-CCGGACAATGAAGAAGCCTTT-3'; (SEQ ID NO: 21)
and

5'-TCTAGCCACAACAGGGTCAAT-3'. (SEQ ID NO: 22)

In a third aspect, the present invention provides recombinant expression vectors comprising the isolated nucleic acid of any embodiment of the third aspect of the invention operatively linked to a promoter. "Recombinant expression vector" includes vectors that operatively link a nucleic acid coding region or gene to any promoter capable of effecting expression of the gene product. The vectors can be used, for example, for transfection of host cells for large scale production of the isolated nucleic acids, or may be used as vector delivery systems in the methods of the invention. The promoter sequence used to drive expression of the disclosed nucleic acid sequences in a mammalian system may be constitutive (driven by any of a variety of promoters, including but not limited to, utilizes the U6 or H1 promoter promoter (to ensure that the shRNA is always expressed), CMV, SV40, RSV, actin, EF) or inducible (driven by any of a number of inducible promoters including, but not limited to, tetracycline, ecdysone, steroid-responsive). The construction of expression vectors for use in transfecting eukaryotic and prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols, pp.* 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a viral vector or a plasmid. Any suitable viral vector may be used, including but not limited to retroviruses, lentiviruses, adenoviruses, adeno-associated viruses, etc.

In a fourth aspect, the present invention provides host cells comprising the recombinant expression vectors disclosed herein, wherein the host cells can be either prokaryotic or eukaryotic. The host cells can be used, for example, in large scale production of the recombinant vectors of the invention. The cells can be transiently or stably transfected if a plasmid vector is used, or may be transiently or stably transduced when a viral vector is used. Such transfection and transduction of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, 2$^{nd}$ Ed. (R. I. Freshney. 1987. Liss, Inc. New York, N.Y.).

In a fifth aspect, the present invention provides pharmaceutical compositions, comprising (a) the isolated nucleic acid of any embodiment of the second aspect of the invention, the recombinant expression vector of any embodiment of the third aspect of the invention, or the recombinant host cell of any embodiment of the fourth aspect of the invention; and (b) a pharmaceutically acceptable carrier.

The pharmaceutical compositions can be used, for example, in the methods of the invention. As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, fumaric, toluenesulfonic, methanesulfonic, nitric, benzoic, citric, tartaric, maleic, hydroiodic, alkanoic such as acetic, $HOOC-(CH_2)_n-COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts. All embodiments of pharmaceutical compositions discussed herein for the methods of the invention can be used in this aspect of the invention.

In a sixth aspect, the present invention provides methods for identifying candidate compounds for treating a tumor, comprising (a) contacting tumor cells capable of expressing QSOX1 with one or more candidate compounds under conditions suitable for expression of QSOX1;

(b) determining a level of QSOX1 expression and/or activity in the tumor cells and comparing to control;

wherein a compound that decreases QSOX1 expression and/or activity in the tumor cells relative to control is a candidate compound for treating a tumor.

Any tumor cell can be used that is capable of expressing QSOX1, either inherently or as a result of transfecting the cell with a QSOX1 recombinant expression vector. In a preferred embodiment, the tumor cell is selected from the group consisting of pancreatic, lung, colon, breast, and prostate tumor cells. In a preferred embodiment, the tumor cells are pancreatic tumor cells, preferably pancreatic adenocarcinoma cells.

Any suitable candidate compound can be used, including but not limited to small molecules, antibodies, aptamers, antisense, siRNA, and shRNA.

As used herein, "inhibit" means at least a 10% reduction in expression and/or activity; preferably at least 20%, 30%, 40%, 50%, 60%, 70%, 80%, 90%, or greater reduction in expression and/or activity.

Any suitable control can be used, including but not limited to tumor cells not treated with test compound, and average expression product levels of QSOX1 in a control cell population. In one embodiment, the control comprises a cell from a normal subject or population (ie: known not to be suffering from a tumor), or from a subject or population of subjects suffering from a tumor, using the same detection assay. In another preferred embodiment, the control comprises a tumor cell contacted with the isolated nucleic acid, shRNA, or expression vector of the invention, to facilitate identifying compounds with increased QSOX1 inhibitory activity than the nucleic acids disclosed herein. The control cell will be of the same type as that assessed from the test subject. In one exemplary embodiment where immunohistochemistry is used to assess QSOX1 expression, a suitable control is normal tissue in a pathological sample.

Any suitable method for determining QSOX1 expression levels may be used, including but not limited to reverse transcription-polymerase chain reaction (RT-PCR), Western blot, in situ hybridization, and immunohistochemical analysis (such as fluorescence in situ hybridization)

Similarly, any suitable method for determining QSOX1 activity levels may be used, including but not limited to an oxygen electrode assay, using the enzymatic activity of QSOX1 to detect structures/compounds that inhibit the ability of QSOX1 to oxidize a known substrate.

Example 1

Pancreatic ductal adenocarcinoma (PDA) is a disease that carries a poor prognosis. It is often detected in stage III resulting in an unresectable tumor at the time of diagnosis. However, even if pancreatic cancer is surgically resected in stage I or II, it may recur at a metastatic site (1, 2). Currently, patients diagnosed with pancreatic ductal adenocarcinoma have less than a 5% chance of surviving past five years (3). Through proteomic analysis of pancreatic cancer patient plasma, we discovered a peptide from QSOX1 that maps back to the C-terminus of the long isoform of QSOX1 (QSOX1-L) (4). Subsequently, we found that QSOX1 is over-expressed in tumor tissue from pancreatic cancer patients, but not adjacent normal tissue (FIGS. 1B & C). These findings led us to hypothesize that over-expression of QSOX1 might be functionally important for tumor cells, prompting further exploration of the role that QSOX1 might play in pancreatic cancer.

QSOX1 belongs to the family of FAD-dependent sulfhydryl oxidases that are expressed in all eukaryotes sequenced to date. As eloquently shown by the Thorpe and Fass laboratories, the primary enzymatic function of QSOX1 is oxidation of sulfhydryl groups during protein folding to generate disulfide bonds in proteins, ultimately reducing oxygen to hydrogen peroxide (5-7). QSOX1 has been reported to be localized to the Golgi apparatus and endoplasmic reticulum (ER) in human embryonic fibroblasts where it works with protein disulfide isomerase (PDI) to help fold nascent proteins in the cell (8, 9).

In the human genome, QSOX1 is located on chromosome 1q24 and alternative splicing in exon 12 generates a long (QSOX1-L) and short (QSOX1-S) transcript (FIG. 1A) (10). Both, QSOX1-S and -L have identical functional domain organization from the amino terminus as follows: two thioredoxin-like domains (Trx1 &2), a helix rich region (HRR) and an Erv/ALR FAD-binding domain (5, 11). QSOX1-L contains a predicted transmembrane domain that is not present in QSOX1-S due to alternative splicing (FIG. 1A) (12). QSOX1 was originally discovered in quiescent human lung fibroblasts and was hypothesized to aid in the transition from $G_0$ to S phase of the cell cycle (13, 14). Thorpe et al. revealed the ability of QSOX1 to efficiently generate disulfide bonds into proteins during folding at rate of 1000 per minute with a $K_M$ of 150 uM per thiol (7). QSOX1 appears to play a significant role in redox regulation within the cell, although the in vivo biological substrates are undefined as well as the functional significance associated with each splice variant.

In the present study, we have begun to analyze the role of QSOX1 in pancreatic tumors using cell lines BxPC3 and Panc-1. We knocked down QSOX1-S and -L protein expression using short hairpin RNAs (shRNA) in an attempt to reveal how pancreatic cancer cells might be affected. We assessed cell growth, cell cycle, apoptosis, invasion and matrix metalloproteinase activity. QSOX1 knock-downs affected tumor cell proliferation, cell cycle and apoptosis. We observed a dramatic decrease in tumor cell invasion when QSOX1 expression was suppressed. Further investigation into the mechanism of invasion revealed that QSOX1 is at least partially responsible for MMP-2 and MMP-9 activity. This is the first report demonstrating a role for QSOX1 in invasion and metastasis.

Material and Methods
Cell Culture

Pancreatic adenocarcinoma BxPC3, PANC-1, CFPac-1, and Capan1 cancer cell lines were cultured in DMEM with 10% fetal bovine serum (FBS) (Gibco). Immortal human non-tumorigenic pancreatic duct epithelial cells (HPDE6) were cultured in Clontech KGM-2 karotinocyte media (Gibco) (19). All cell lines were grown at 37° C. with 5% $CO_2$. Cell lines are tested monthly for mycoplasma contamination using, Venor GeM™ Mycoplasma Detection Kit, PCR based from Sigma.
Immunohistochemistry (IHC)

Immunohostochemistry on patients who underwent surgical resection was performed in the exact same manner as previously described in Kwasi et al (4).
Generation of Short hairpin (sh) RNA and Lentiviruses Production Three different shRNA for QSOX1 were obtained through DNASU (http://dnasu.asu.edu)(20) already in the lentiviral pLKO.1-puromycin selection vector. QSOX1 sh742, 5'-CCGG<u>GCCAATGTGGTGAGAAAGTTTCTCGAGAAACTTTCTCACCACATTGGCTTTTTG</u>-3' (SEQ ID NO: 26) (sense), QSOX1 sh528, 5'-CCGG<u>ACAATGAAGAAGCCTTT</u>-3' (SEQ ID NO: 21) (sense), QSOX1 sh616, 5'-<u>TCTAGCCACAACAGGGTCAAT</u>-3' (SEQ ID NO: 22) (sense) and shScramble with target sequence 5'-<u>TCCGTGGTGGACAGCCACATG</u>-3' (SEQ ID NO: 29) was obtained from Josh LaBaer's laboratory at Arizona State University. The target sequence is underlined and each vector contains the same supporting sequence surrounding the target sequence.

Lentiviruses containing sh742, sh528, sh616 and shScramble were produced using 293T cells. 293T cells were seeded at $1.5 \times 10^6$ cells per well in 2 mL media lacking antibiotics using a 6 well plate format and incubated at 37° C., 5% $CO_2$ for 24 hrs. The following day the 293T cells were transfected with 2500 ng shRNA maxi-prepped plasmid DNA (Sigma GeneElute™ HP Plasmid Maxiprep Kit), 500 ng VSVg, 2500 ng d8.91 (gag-pol) in LT1 transfection reagent from Mims Bio (Madison, Wis.) and centrifuged at 1000 g for 30 minutes and incubated as 37° C., 5% $CO_2$ for 24 hrs at in media lacking antibiotics. The next morning media containing lentivirus was collected and replaced with complete media. Supernatants (2.5 ml) from transfected 293T cells producing each lentivirus were collected every 24 hours for a total of 72 hours, combined and stored at −20° C.
Generation of shQSOX1-Transduced Tumor Cell Lines Stable transduction of sh742, sh528, sh616 and shScramble into BxPC-3 and Panc-1 cell lines was performed by first seeding the cells at $8 \times 10^5$ cells/well in a 6 well plate and incubating overnight. The next day the cells were transduced by adding 8 ug/mL polybrene (Millipore) and 200 ul sh742, sh528, sh616 and shScramble lentivirus media from 293T cells to each well. The cells were spun at 1000 rpm for 30 minutes and then incubated for 24 hours. The following day fresh DMEM with 10% FBS was added, containing 1 ug/mL puromycin (Sigma), to select for the transduced cells QSOX1 knockdown was measured by western blot.
SDS-PAGE-Western blotting Western blotting was performed using cell lysates from HPDE6, BxPC3, Panc-1, Capan1 and CFPac1 cells as well as patient 1010 and 1016 tumor and adjacent normal enzymatic supernatant. Cell lysates were generated by harvesting $2.5 \times 10^6$ cells by centrifugation followed by lysis using RIPA buffer (50 mM Tris-HCl, pH 7.4, 150 mM NaCl, 1 mM EDTA, and 1% Triton X-100) with 1× SigmaFAST™ Protease Inhibitor Cocktail Tablet, EDTA Free. Protein in the cell lysate was measured using the micro BCA protein assay kit (Thermo Scientific). All samples were then normalized to 2 ug/mL (20 ug total protein per lane). Samples were run on 10% SDS-polyacrylamide gels then transferred onto Immun-Blot™ PVDF Membranes (Bio-Rad). Rabbit polyclonal anti-QSOX1 (ProteinTech), rabbit polyclonal anti-Bactin and anti-alpha-tubulin (Cell Signaling), and rabbit polyclonal anti-MMP-2 and -9 (Sigma) antibody was diluted 1:1000, 1:1000, and 1:500 respectfully, in 0.1% BSA in 1×TBS+ 0.01% Tween-20 and incubated for overnight. Goat anti-rabbit IgG-alkaline phosphatase or HRP secondary antibody was used at a 1:5000 dilution and incubated with the blot for 1 h followed by washing. BCIP/NBT substrate (Pierce Chemical, Rockford, Ill.) was added and the blot was developed at room temperature (RT) for approximately 1 hour, in samples incubated in alkaline phosphatase secondary antibody. For samples incubated in goat anti-rabbit HRP secondary the blots were developed using Novex ECL Chemiluminescent Substrate Reagent Kit. Quantification of band intensity was measured using Image J and is presented as percent change from the scrambled shRNA control. Full gel images are available in the supplemental material. All gel images were annotated and processed using Photoshop software.

MTT (3-(4,5-Dimethylthiazol-2-yl)-2,5-diphenyltetrazolium bromide) Assay

Cells were seeded at $3 \times 10^3$ cell/well in a 96-well plate in triplicate and incubated at 37° C., 5% $CO_2$ over the course of 5 days. The MTT assay was performed on days 1, 2 and 5 according to the manufacturers' instructions (Invitrogen-Molecular Probes, Vybrant MTT Cell Proliferation Assay Kit). Results are presented as mean+/−S.D. Student's two tailed T-test was performed to determine significance.

Annexin V/Propidium Iodide Apoptosis Analysis

Apoptosis analysis was performed according to the manufacturer's instructions (FITC Annexin V Apoptosis Detection Kit I, BD Pharmingen). Briefly, cells were seeded at equal densities in a 25 $cm^2$ flask until they reached 60-80% confluency. The cells were then washed with cold PBS, counted, and normalized to $1 \times 10^6$ cell/ml in 1× Annexin V Binding Buffer. Next, $1 \times 10^5$ cells were then transferred to a separate tube and 5 µl of FITC Annexin V and 5 µl of Propidium Iodide were added to each sample. The samples were gently vortexed and incubated for 15 min at RT in the dark. Lastly, 400 µl of 1× Binding Buffer was added to each sample and the samples were analyzed by flow cytometer (Becton Dickinson FACS-calibur™ Flowcytometer) with 1 hr. Each sample was performed in triplicate.

Gelatin Zymography

The identification of matrix metalloproteinases (MMP) was performed using gelatin zymography. Zymography experiments were performed as follows. Untreated BxPC3 and Panc-1 cells as well as transduced cells were seeded at $5 \times 10^5$ cells/well (12 well plates) in DMEM with 10% FBS. The next day, cells were then washed with 1×PBS and the media was changed to serum free DMEM and incubated for 24 hours before being collected and protein concentrations determined using a BCA assay. Gelatin zymography was performed with a 10% polyacrylamide gel containing gelatin solution in place of water (0.8 mg/mL Gelatin, 0.15 M Tris pH 8.8, 30% acrylamide-bis, 50% glycerol, 10% SDS, 10% APS, and TEMED) (21). A volume of equal concentrations of serum free conditioned media were loaded under non-denaturing conditions into the 10% polyacrylamide-gelatin gel to separate proteins secreted by the tumor cells and to detect the presence of gelatin degrading MMPs. Electrophoresis was performed at a constant voltage of 150 V for 60 min. Gels were washed in renaturing buffer (25% Triton X-100 in water) for 30 min at RT with gentle shaking. The gels were then equilibrated in developing buffer (50 mM Tris-base, 6.3 g/L Tris-HCl, 0.2 M NaCl, 5 mM $CaCl_2$, and 0.02% Triton X-100) for 30 min at RT with gentle shaking Fresh developing buffer was then added to the gels and they were incubated overnight at 37° C. The gels were then stained with Simply-Blue™ Safe Stain (Invitrogen) for 20 minutes at RT, then destained overnight in dd$H_2$O at RT. The presence of MMP was detected by the lack of staining indicating digestion of gelatin. The negative control was performed by adding, 50 mM Ethylene Diamine Tetra Acetic Acid (EDTA), to both the renaturing buffer and the developing buffer to block the MMP activation. Quantification of band intensity was measured using Image J and is presented as percent change from the scrambled shRNA control.

RNA Isolation and cDNA Synthesis

Total RNA isolation was performed according to the manufactures instructions for animal cells using spin technology (RNeasy™ Mini Kit, Qiagen). After RNA was isolated from each sample was reverse transcribed with gScript™ cDNA Sythesis Kit, Quanta Biosciences according to the manufactures instructions.

Quantitative Real Time PCR (qPCR)

The relative level of GAPDH, QSOX1-L, QSOX1-S, MMP-2, and MMP-9 were analyzed in each sample by qPCR. Each cDNA sample was normalized to 100 ng/µl in molecular grade water along with 100 nM final concentration of each primer and 1× final concentration of PerfeCta™ SYBR Green Fast Mix, ROX to a final volume of 20 µl. qPCR was performed using, PerfeCTa™ SYBR Green FastMix, ROX from Quanta Biosciences on a ABI7900HT thermocycler, Applied Biosystems Inc. Reaction Protocol: Initial Denaturation −95° C. for 3 min; PCR Cycling (40 cycles) 1.) 95° C., 30 sec. 2.) 55° C., 30 sec. 3.) 72° C., 1 min; Melt Curve (Dissociation Stage). The primer sequences for the genes analyzed are:

```
                                        (SEQ ID NO: 30)
GAPDH Forward 5'-GGCCTCCAAGGAGTAAGACC;

(SEQ ID NO: 31)
GAPDH Reverse 5'-AGGGGTCTACATGGCAACTG;

(SEQ ID NO: 32)
QSOX1-S Forward 5'-TGGTCTAGCCACAACAGGGTCAAT;

(SEQ ID NO: 33)
QSOX1-S Reverse 5'-TGTGGCAGGCAGAACAAAGTTCAC;

(SEQ ID NO: 34)
QSOX1-L Forward 5'-TTGCTCCTT GTCTGGCCTAGAAGT;

(SEQ ID NO: 35)
QSOX1-L Reverse 5'-TGTGTCAAAGGAGCTCTCTCTGTCCT;

(SEQ ID NO: 36)
MMP-2 Forward 5'-TTGACGGTAAGGACGGACTC;

(SEQ ID NO: 37)
MMP-2 Reverse 5'-ACTTGCAGTACTCCCCATCG;

(SEQ ID NO: 38)
MMP-9 Forward 5'-TTGACAGCGACAAGAAGTGG;
and (SEQ ID NO: 39)
MMP-9 Reverse 5'-CCCTCAGTGAAGCGGTACAT.
```

Each reaction was performed in triplicate with the data representing the averages of one experiment.

In the shRNA experiment, expression of MMPs was normalized to the non-targeted GAPDH to determine ΔCq. ΔCq replicates were then exponentially transformed to the ΔCq expression after which they were averaged±standard deviation. The average was then normalized to the expression of the shScramble control to obtain the ΔΔCq expression. Significance was determined using the student two tailed T-test.

Matrigel™ Invasion Assay

Invasion assays were performed using BD BioCoat™ BD Matrigel™ Invasion chambers with 8.0 μm pore size polyethylene terephthalate (PET) membrane inserts in 24-well format. The assay was performed according to the manufacturers' instructions (BD Bioscience). $4 \times 10^4$ cells/well were seeded into the inner Matrigel™ chamber in serum free DMEM. The outer chamber contained 10% FBS in DMEM. BxPC3 and Panc-1 cells were incubated for 24 hours at 37° C., 5% $CO_2$. Cells that invaded through the Matrigel™ and migrated through the pores onto the bottom of the insert were fixed in 100% methanol and then stained in hematoxylin (Invitrogen). The total number of invading cells were determined by counting the cells on the underside of the insert from three wells (6 fields per insert) at 10×, 20× and 40× magnification and the extent of invasion was expressed as the mean+/−S.D. Significance was determined using the Student's two tailed T-test. Results presented are from one of three independent experiments.

Results

Detection of QSOX1 by Immunohistochemistry and Western Blot

To begin to determine the frequency of expression of QSOX1 in human PDA, QSOX1 expression was assessed in 4 different pancreatic tumor cell lines, an immortal non-tumorigenic cell line, HPDE6, 37 tumor tissue sections from patients with PDA, and tumor and adjacent normal tissue from two patients, 1016 and 1010 (FIGS. 1B, C, and D). 29 of 37 tumor tissues were positive for QSOX1 expression, suggesting it is a commonly over-expressed protein. To determine which splice variant was more prevalent in our IHC images we analyzed tumor as well as adjacent normal tissue from 2 patients by western blot (FIG. 1C). Our results revealed that QSOX1-S is the dominant splice variant expressed also corroborating our IHC results that revealed an increase in QSOX1 expression in tumor samples. While our adjacent normal samples indicate a high level of QSOX1 expression, it is hard to determine if there was any tumor tissue contaminating our normal sample, which would account the increase in QSOX1 expression. Western blotting analysis shows that 4 pancreatic tumor cell lines, BxPC3, Panc-1, Capan1 and CFPac1 strongly express QSOX1-S and weakly express the longer splice variant, QSOX1-L. HPDE6, an immortal, non-tumorigenic pancreas epithelial cell line, shows weak expression of QSOX1-S and no expression of QSOX1-L (FIG. 1D).

The results of this experiment begin to provide some information about the frequency and distribution of QSOX1 expression. First, QSOX1 appears to be a commonly over-expressed protein in PDA (FIG. 1B-C). Second, QSOX1 protein expression in adjacent normal 1016, 1010, and HPDE6, a non-tumorigenic pancreatic duct cell line, is much weaker than it is in the patient tumor samples and four malignant pancreatic tumor cell lines. This may suggest that QSOX1 provides some advantage to malignant cells that non-malignant cells do not require.

QSOX1 Promotes Tumor Cell Proliferation

Figure 2:
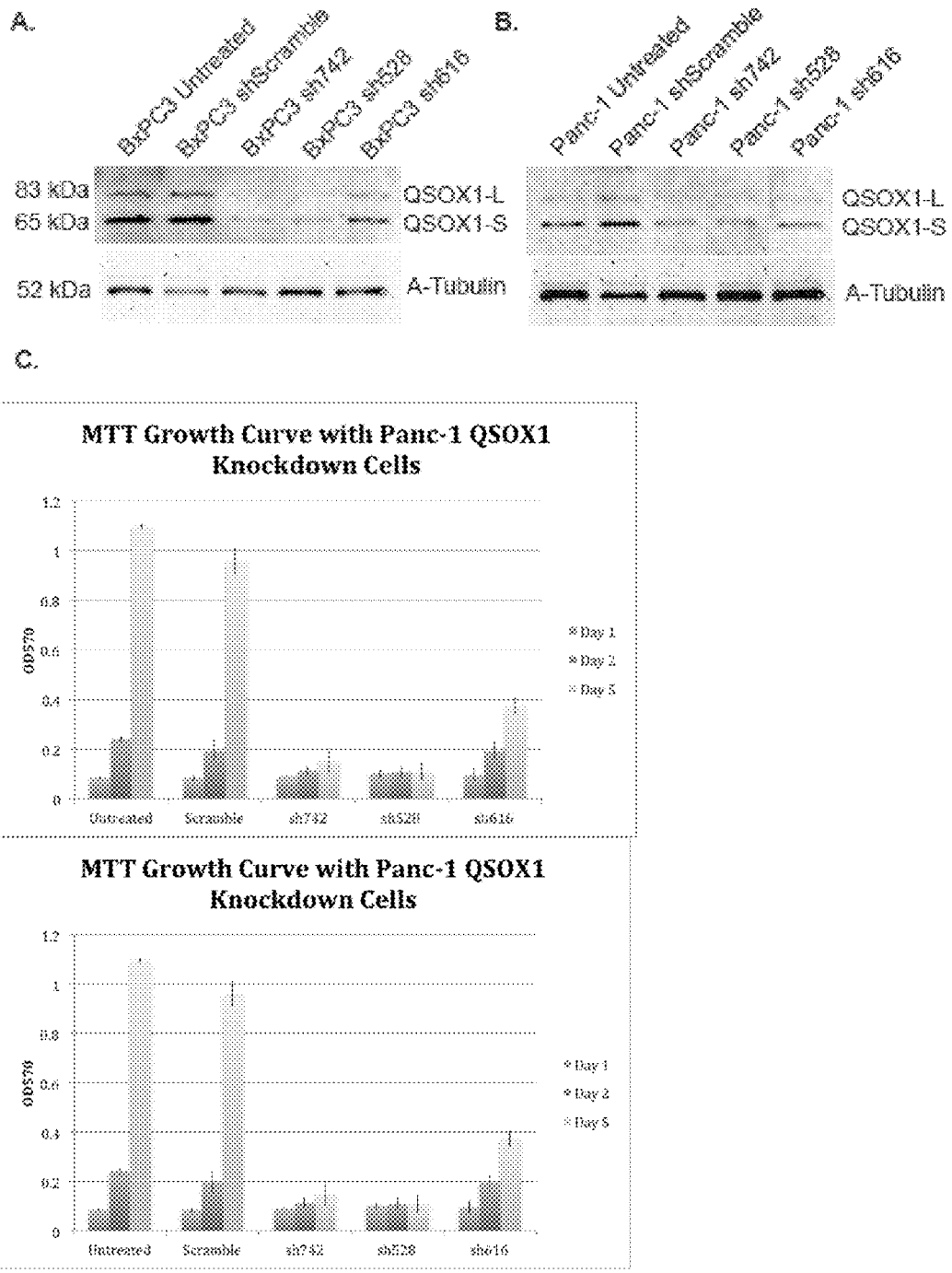
FIG. 2: Reduced expression of QSOX1 in BxPC3 and Panc-1 cells leads to a significant decrease in cell growth. To determine the phenotype presented due to the expression of QSOX1 in tumor cells we employed shRNA specific to QSOX1 to reduce the expression of QSOX1 in A.) BxPC3 (Percent Decrease in sh742-56%; sh528-40%; sh616-28%) and B.) Panc-1 (Percent Decrease in sh742-64%; sh528-46%; sh616-18%) cells and further evaluated cell growth, cell cycle, apoptosis, and invasion/metastasis. C.) MTT assay on shRNA treated BxPC3 and Panc-1 cells assayed on day 1, 2, and 5. Data represents averages±standard deviation. Significance *, P<0.05; **, P<0.01.

To examine the advantage that QSOX1 provides to tumor cells we inhibited QSOX1 expression in BxPC3 and Panc-1 cells using 3 shRNA constructs: sh742, sh528 and sh616. shScrambled was generously provided by Dr. Joshua LaBaer. Lentiviruses containing each shRNA were generated as described in "Methods." BxPC3 and Panc-1 cells were transduced with each sh-lentivirus (shQSOX1) to evaluate the effects of QSOX1 knockdown on tumor cell growth. To demonstrate that the shQSOX1 are active in both cell lines, FIG. 2A-B shows reduced protein expression of both isoforms of QSOX1 in BxPC3 and Panc-1 tumor cell lines compared to scrambled shRNA in western blot analysis. This experiment demonstrates that sh742, sh528 and sh616 knock down of QSOX1-S expression in BxPC3 cells was 56%, 40% and 28%, respectively; for Panc-1 cells the knock down was 64%, 46% and 18%, respectively (FIG. 2A-B).

ShQSOX1-transduced BxPC3 and Panc-1 cells exhibited a decrease in cell growth compared to shScrambled controls in an MTT assay (FIG. 2C) and by trypan blue viable cell dye (not shown). We seeded an equal number of shScramble, sh742, sh528 and sh616 cells in 96 well plates and quantified the proliferation rate by measuring mitochondrial metabolism on days 1, 2 and 5. While on day 1 there was no change, day 2 presented a minor decrease in cell growth by day 5 BxPC3 sh742, sh528 and sh616 showed a 65%, 60% and 37% decrease, while in Panc-1 sh742, sh528 and sh616 there was a 84%, 88% and 61% decrease. Live cell counts using trypan blue confirmed the MTT assay (not shown).

Cell Cycle and Apoptosis Analysis

Previous work has correlated QSOX1 expression with the quiescent stage, $G_o$, of the cell cycle (10), leading us to hypothesize if the shQSOX1-mediate decrease in cell proliferation was the result of abnormal regulation of the cell cycle or an increase in apoptosis. To address this hypothesis, propidium iodide (PI) was used in flow cytometry to evaluate the effects of shQSOX1 on cell cycle. Our results indicate that suppression of QSOX1 expression did modulate cell cycle in both BxPC3 and Panc-1 compared to our untreated and scrambled control (data not shown). The results show that the reduced expression of QSOX1 on cell cycle could be cell dependent. BxPC3 showed an increase in $G_1$ and a significant decrease in S, while Panc-1 cells showed a significant decrease in $G_1$ but no changes in S.

We further evaluated if the decrease in cellular proliferation mediated by shQSOX1 was due to an increase in apoptotic cell death. To assess apoptosis, BxPC3 and Panc-1 cells transduced with shScramble, sh742, sh528 and sh616 were stained with annexin-V and PI. Compared to untreated and shScramble a consistent increase of 2-8% in early and late apoptosis (Annexin-V single and double positive) was observed for each of the shQSOX1 constructs in BxPC3 and Panc-1 cells. Indicating that the reduced expression of QSOX1 does lead to cell death but does not entirely account for the dramatic decrease in cellular proliferation. This data also agrees with our viable cell count revealing a largely nonsignificant decrease in shQSOX1 viable cells compared to untreated and shScramble controls.

Role of QSOX1 in Tumor Cell Invasion

For a tumor cell to invade other tissues as part of the metastatic process, the cell must first degrade basement membrane components such as laminin, collagen and fibronectin before it can migrate into the blood stream and re-establish itself in a distant organ (3). To evaluate whether over-expression of QSOX1 in BxPC3 and/or Panc-1 cells plays a role in metastasis we performed invasion assays over an 18-hour period. Untreated, shScramble, sh742, sh528 and sh616-transduced cells were plated in serum-free medium on Matrigel™-coated, 8 um pore inserts. Inserts were placed into wells containing 10% FBS in DMEM. After 18 hours of incubation, tumor cells that had degraded Matrigel™ and migrated through 8 um pores onto the underside of the insert were counted (FIG. 4A-B). Our results clearly demonstrate that knockdown of QSOX1 expression in tumor cells leads to a dramatic decrease in the number of pancreatic tumor cells that degrade Matrigel™ and migrate through the insert into nutrient rich media.

Mechanism of Invasion

Since knock-down of QSOX1 protein expression in pancreatic tumor cells lines decreases invasion through Matrigel™, it was important to determine the mechanism of inhibition of the invasive process. MMP-2 and -9 are key contributors of invasion and metastasis in pancreatic cancer (2). Both, pro-MMP-2 and -9 mRNA and protein levels are elevated in pancreatic tumors, and activated MMP-2 (a-MMP2) appears to be key contributors of metastasis in PDA (2, 22). Because QSOX1 has been suggested to be secreted into the extracellular matrix where MMPs are thought to be activated, we hypothesized that QSOX1 might help activate MMP-2 and -9 proteins. Untreated BxPC3 and Panc-1 cells, as well as transduced shScramble, sh742, sh528 and sh616 were incubated for 18-24 hours in serum free media after which supernatants were collected and subjected to gelatin-SDS-PAGE. Gelatin zymography was performed to determine if QSOX1 plays a role in secretion and/or activation of MMPs.

Our first observation from this experiment is that BxPC3 and Panc-1 have very different zymographic profiles. BxPC3 supernatants contain MMP-9 homodimer (130 kDa), a large amount of proteolytically active pro-MMP-9 (92 kDa) with lesser concentrations of pro-MMP-2 (72 kDa) and a-MMP-2 (66 kDa). Panc-1 supernatants contain less prominent MMP-9 homodimer, pro-MMP-9 (92 kDa) and a large amount of proteolytically active pro-MMP-2 (72 kDa), unlike BxPC3 cells.

Supernatants from BxPC3 cells transduced with sh742, sh528 and sh616 showed a 65%, 47% and 10% decrease, respectfully, in pro-MMP9 compared to shScramble (FIG. 5A). Supernatants from Panc-1 cells tranduced with sh742, sh528 and sh616 showed a 70%, 56% and 15% decrease, respectfully, in pro-MMP-2. Thus, decreases in the proteolytic activity of MMP-2 and -9, using gelatin as a substrate, provide a mechanism for the shQSOX1-mediated suppression of invasion through Matrigel™.

To confirm our gelatin zymography results we used western blot analysis of BxPC3 and Panc-1 serum free conditioned media to probe for MMP-2 and -9 (FIG. 5C). While our results indicate a slight decrease in MMP-2 and -9 (between 1 and 10% decrease using densitometry analysis) in BxPC3 and Panc-1 shQSOX1 treated cells it is nowhere near the level shown using gelatin zymography. This could be explained as a difference between a functional assay, gelatin zymography, and a purely quantitative assay such as western blot.

Figure 5:
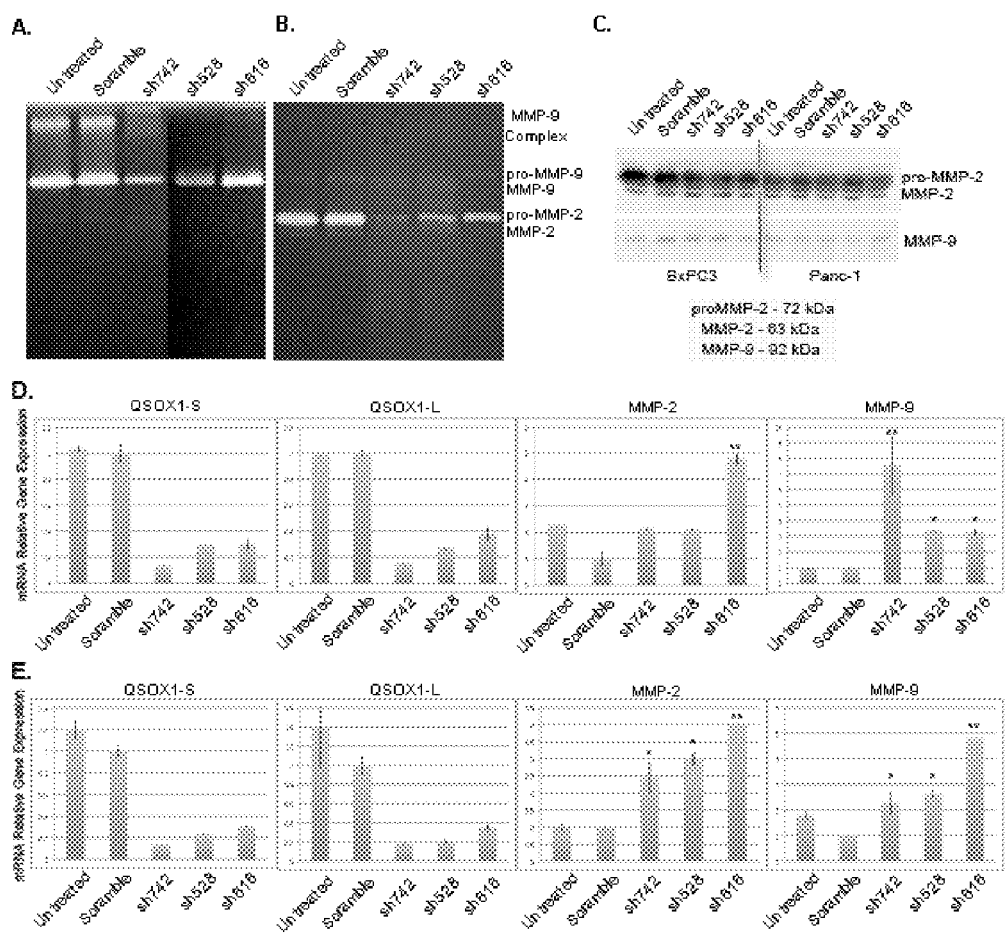
FIG. 5: Reduced expression of QSOX1 leads to a decrease in secreted proMMP-9 in BxPC3 and proMMP-2 Panc-1 cells. Gelatin zymography of A.) BxPC3 and B.) Panc-1 conditioned media showing a decrease in MMP-9 homodimers (MMP-9 Complex) (240 and 130 kDa), pro-MMP9 (92 kDa), pro-MMP2 (72 kDa) and active MMP-2 (a-MMP2, 66 kDa). Using Image J we were able to quantify the percent decrease in proMMP-9 expression in BxPC3 (Decrease in QSOX1, sh742-65%; sh528-47%; sh616-10%) and Panc-1 proMMP-2 (Decrease in QSOX1, sh742-70%; sh528-56%; sh616-15%). C.) Western blot analysis of MMP-2 and -9 on conditioned serum free media from shRNA treated BxPC3 and Panc-1 cells. D.) The effect of shRNA mediated knockdown of QSOX1 on the expression of QSOX1-S, QSOX1-L, MMP-2, and MMP-9 in BxPC3 and Panc-1 shRNA treated cells was analyzed by quantitative real time PCR analysis. The graph represents relative gene expression calculated as $\Delta\Delta Cq$ using GAPDH as the endogenous reference gene.

To extend our hypothesis that QSOX1 is influencing MMPs post-translationally, we performed quantitative real time PCR (QRTPCR) on MMP-2 and MMP-9 comparing the transcripts from shQSOX1 transduced cell lines with shScrambled. FIG. 5 demonstrates that MMP-2 and -9 RNA increased in the shQSOX1 transduced cells compared to control cells. This result adds confidence to our hypothesis that QSOX1 does not transcriptionally suppress MMP production, rather it post-translationally suppresses MMP activity. It also diminishes the possibility that shQSOX1 RNAs are suppressing MMP transcription due to off-target effects.

Discussion

The mortality rate for patients diagnosed with pancreatic cancer has remained stagnant for the last five decades despite advanced surgical procedures and improvements in chemotherapeutics (23). Because most patients present with advanced metastatic disease, it is critical to understand the properties of invasive pancreatic tumors. Discovery and subsequent study of factors that contribute to tumor cell invasion provide an opportunity to develop therapeutics that could be used alone or in combination with other anti-neoplastic agents. Prior to our report (4), it was not previously known that QSOX1 was over-expressed in pancreatic tumors. The results presented in FIG. 1 suggest that QSOX1 is a commonly over-expressed protein in PDA, making it a potential target. To extend those initial findings we began to investigate why pancreatic tumors over-express QSOX1, and mechanistically, what advantage it affords tumors.

Figure 3:
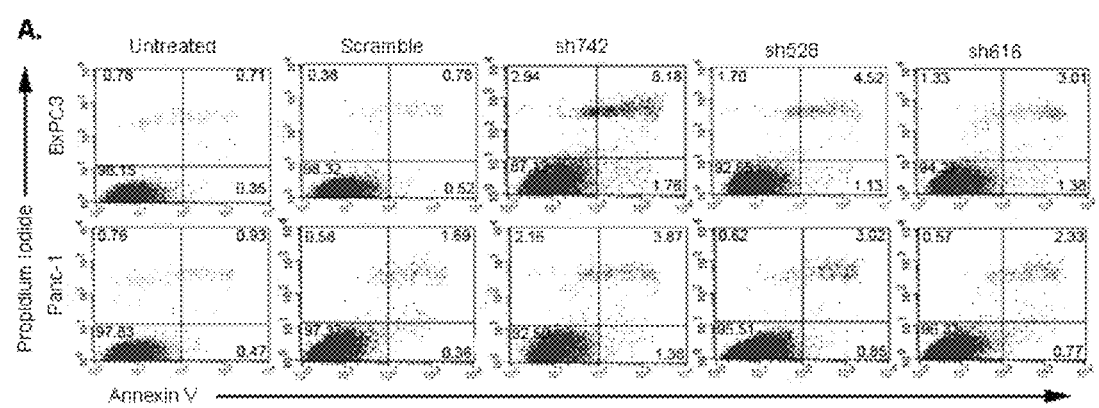
FIG. 3: Reduced expression of QSOX1 in BxPC3 and Panc-1 cells leads to an increase in annexin V/propidium iodide positive cells. A.) Apoptosis Analysis (Annexin V/Propidium Iodide) was performed on BxPC3 and Panc-1 cells in which QSOX1 was reduced using shRNA. Plots show representative data from one of three individual experiments for gated samples of Untreated, Scramble, sh742, sh528 and sh616. The percentages represent the number of cells that are annexin V positive (Lower Right), annexin V/propidium iodide double positive (Upper Left), or propidium iodide positive (Upper Right). Data was calculated using Cell Quest Pro software.

Tumor cells in which QSOX1 protein expression was suppressed by shQSOX1 grew more slowly than the shScrambled and untreated controls as measured by an MTT assay, while the results with our strongest shQSOX1, sh742, show a greater that 50% decrease in cell growth in both BxPC3 and Panc-1 cells (FIG. 2C). Our attempt to try and explain the decrease in proliferation as a result of abnormal cell cycle regulation or an increase in apoptosis do not show a similar level of change that can solely explain our MTT results (FIG. 3, S2). Contrary to previous statements implicating QSOX1 as a cell cycle regulator (24), our results suggest that while the loss of QSOX1 in Panc-1 cells shows a consistent decrease in $G_1$, there is no where near that effect when we analyzed BxPC3 cells suggesting that the role of QSOX1 could be cell type and tumor stage dependent, as a result of the different substrates available (S2). Our results likely conflict because we assessed the effect of QSOX1 on pancreatic tumor cell growth, not fibroblasts where QSOX1 was initially described (5, 24).

The same statement can be made in regards to the loss of QSOX1 directly affecting apoptosis. While our strongest knock-down, sh742, does show at its greatest an 8% increase in annexin V/propidium iodide double positive cells it is not enough to explain the dramatic decrease in cellular proliferation (FIG. 3). There are numerous proteins within the cell that assist in disulfide bond formation that may compensate for the loss of QSOX1 such as protein disulfide isomerase (PDI), thioredoxin, glutathione and members of the Ery family of sulfhydryl oxidases (25). There are no known preferred substrates of QSOX1 although speculation based on the function of QSOX1 as well as the known substrates that correspond to QSOX1 functional domains, leads us to believe that there are a broad spectrum of possible substrates and therefore the role that QSOX1 plays in tumor cell progression would most likely be influenced by the substrates with the greatest affinity for QSOX1. Compensation by these other oxidases could help explain why the loss of QSOX1 does not lead to significant alterations in the cell cycle and apoptosis. It is also possible that suppression of QSOX1 activity does not induce apoptosis, but results in other phenomena such as anoikis or autophagy (26). We may investigate these possibilities in future studies.

Figure 4:
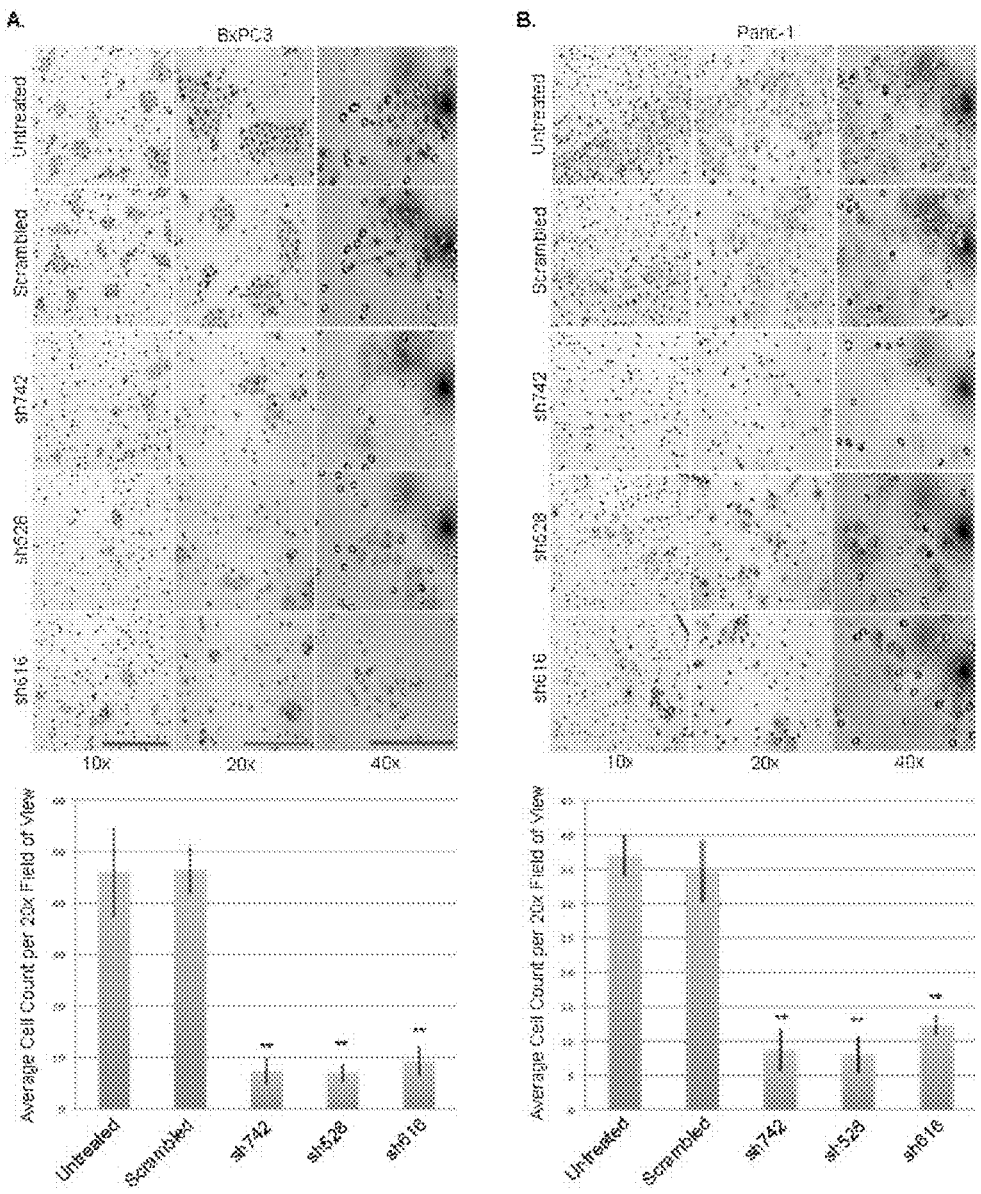
FIG. 4: Reduced expression of QSOX1 in BxPC3 and Panc-1 cells leads to a significant decrease in cellular invasion. A.) Untreated BxPC3 and B.) Untreated Panc-1 cells were treated with Scramble, sh742, sh528 and sh616 shRNA's specific for QSOX1 and seeded in the top chamber of Matrigel™ invasion wells and allowed to incubate for 18 hours. Representative 10×, 20×, and 40× images are presented. In the BxPC3 sh742, sh528 and sh616 treated cells there was an 84%, 84%, and 79% decrease in cells that were able to break down the basement membrane components of the Matrigel™ and invade to the underside of the membrane, respectively. While in Panc-1 sh742, sh528 and sh616 cells there was a 76%, 76%, and 63% decrease in cells that were able to degrade the Matrigel™ and invade through the membrane. Graphs represent average±standard deviation (BxPC3 n=6; PANC-1 n=3), significance *, P<0.05, **, P<0.005.

Another hallmark of cancer is invasion. Since suppression of QSOX1 did not appear to play a major role in tumor cell growth, we hypothesized that the over-expression of QSOX1 in pancreatic tumor cells may contribute to their ability to degrade basement membranes, leading to an invasive and metastatic phenotype. We discovered that suppression of QSOX1 protein resulted in a dramatic reduction in the ability of both BxPC3 and Panc-1 pancreatic tumor cells to invade through Matrigel™ in vitro (FIG. 4). It is clear through these results that there are clear differences between BxPC3 and Panc-1 ability to degrade basement membrane components and invade. This could be due to a myriad of factors such as the proteases secreted, the stage of the tumor and genetic differences between the two cells lines (27). To determine if this reasoning was correct, we performed gelatin zymography as a way to analyze the matrix metalloproteinase activity.

As a sulfhydryl oxidase, it is unlikely that QSOX1 would directly degrade basement membrane components. Therefore, we hypothesized that MMPs serve as a substrate of QSOX1 while the MMPs are folding and undergoing activation as they are secreted from tumor cells. If true, suppression of QSOX1 would lead to a decrease in MMP functional activity, though not necessarily the amount of MMPs produced or secreted. Although the MMP profiles of BxPC3 and Panc-1 cells differ as seen in FIGS. 5A and B, we found that suppression of QSOX1 leads to a decrease in pro-MMP-2 and -9 activity. MMPs are zinc-dependent proteolytic enzymes that degrade ECM components (22). There are 23 known human MMPs as well as 4 known tissue inhibitors of MMPs (TIMP) that aid in regulating the expression and activation of these proteolytic enzymes (22). The expression patterns of MMPs are variable depending on tumor type, and even individual cell line.

In pancreatic cancer the majority of MMPs are secreted in their inactive form and activated extracellularly (28). Activation of MMPs occurs either through the release of a covalent $Cys^{73}$—$Zn^2$ bond ("Cysteine Switch") or through cleavage and activation by plasmin, serine proteases, and other MMPs or TIMPs (21, 28). MMP-2 and -9 have been found to play an important role in pancreatic cancer progression with 93% of tumors expressing MMP-2 compared to normal tissue (28). While reports implicating MMP-9 in the progression of pancreatic cancer are limited, Tian reported the proteomic identification of MMP-9 in pancreatic juice from patients with pancreatic ductal adenocarcinoma (29). Pryczynicz et al. also found a relationship between MMP-9 expression and lymph node metastases (30). Numerous reports implicate MMP-2 as a prominent protease responsible for pancreatic tumor metastasis (2, 22, 28).

One of the benefits of gelatin zymography is that it a.) provides a functional measure of the activities of MMPs able to degrade gelatin and b.) differentiates each precursor and active MMP by molecular weight (21, 31). A limitation of the zymography shown here is that it is limited to MMPs whose substrate is gelatin. It is possible that QSOX1 is involved in activation of other MMPs with different substrates. This will be investigated in future work.

Following up on our initial hypothesis regarding MMP activation by QSOX1 we performed a western blot analysis on the same serum free conditioned media that was used to perform gelatin zymography. Our result revealed that the overall levels of secreted MMP-2 and -9 are nearly equal among the untreated, shScramble and shQSOX1 treated samples leading us to further hypothesize that QSOX1 is involved in the proper folding of MMPs before they are secreted and that the loss of QSOX1 leads to proteolytically inactive MMPs as shown in FIGS. 5A, B and C. To further confirm that what we are observing is a post-translational event we performed qPCR on BxPC3 and Panc-1 shQSOX1 treated cells (FIG. 5D-E). Our observation was surprising in that we are able to show that there is an overall increase in the transcription of MMP-2 and -9. This result led us to hypothesize that the cell is transcriptionally attempting to compensate for the proteolytically inactive MMPs through an as yet undetermined mechanism.

QSOX1 was previously reported by our group to be over-expressed in patients diagnosed with pancreatic cancer (4), and that a peptide from the QSOX1 parent protein is present in plasma from patients with PDA. In the present study we demonstrated for the first time that expression of QSOX1 in pancreatic tumor cells directly contributes to an invasive and potentially metastatic phenotype through the activation of MMP-2 and -9 through an as yet undetermined mechanism. It is not known if QSOX1 is solely responsible for the proper folding of MMPs intracellularly, or if it cooperates with protein disulfide isomerase while MMPs are folding in the ER and golgi. Since MMPs are secreted extracellularly where they may undergo autoactivation or cleavage with proteases such as plasmin, it is possible that QSOX1-S activates them in the extracellular environment.

At this point, the post-translational mechanism by which QSOX1 activates MMPs is not clear. Our results indicate that MMP-2 and -9 RNA increased in shQSOX1 transduced cells. We expected no difference in MMP levels, but an increase might suggest that the cells are attempting to compensate for the lack of MMP activity through a feedback loop (32, 33). Although we hypothesize that QSOX1 may activate MMPs directly by involvement in the cysteine switch activation mechanism (21, 28), ROS produced by QSOX1 may be indirectly activating MMPs, as MMP activation has been reported to depend on an oxidative environment (32, 33).

Our results underscore the need to further understand the role that QSOX1 plays in tumor and normal cells, and how at the molecular level, it activates MMPs. This information will be useful during development of inhibitors of QSOX1 that may work upstream of individual MMPs.

References for Example 1

1. Bardeesy N, DePinho R A. Pancreatic cancer biology and genetics. Nature Publishing Group 2002; 12:897-909.
2. Koshiba T, Hosotani R, Wada M, Miyamoto Y, Fujimoto K, Lee J U, et al. Involvement of matrix metalloproteinase-2 activity in invasion and metastasis of pancreatic carcinoma. Cancer; 1998. p. 642-50.
3. Strimpakos A, Saif M W, Syrigos K N. Pancreatic cancer: from molecular pathogenesis to targeted therapy. Cancer Metastasis Rev 2008; 3:495-522.
4. Antwi K, Hostetter G, Demeure M J, Katchman B A, Decker G A, Ruiz Y, et al. Analysis of the plasma peptidome from pancreas cancer patients connects a peptide in plasma to overexpression of the parent protein in tumors. J Proteome Res 2009; 10:4722-31.
5. Coppock D L, Cina-Poppe D, Gilleran S. The quiescin Q6 gene (QSCN6) is a fusion of two ancient gene families: thioredoxin and ERV 1. Genomics 1998; 3:460-8.
6. Coppock D. Regulation of the Quiescence-Induced Genes: Quiescin Q6, Decorin, and Ribosomal Protein S29. Biochemical and Biophysical Research Communications 2000; 2:604-10.
7. Heckler E J, Alon A, Fass D, Thorpe C. Human quiescin-sulfhydryl oxidase, QSOX1: probing internal redox steps by mutagenesis. Biochemistry 2008; 17:4955-63.
8. Coppock D L, Thorpe C. Multidomain flavin-dependent sulfhydryl oxidases. Antioxid Redox Sign 2006; 3-4:300-11.
9. Hoober K L, Thorpe C. Flavin-dependent sulfhydryl oxidases in protein disulfide bond formation. Methods Enzymol 200230-4.
10. Thorpe C, Hoober K L, Raje S, Glynn N M, Burnside J, Turi G K, et al. Sulfhydryl oxidases: emerging catalysts of protein disulfide bond formation in eukaryotes. Arch Biochem Biophys 2002; 1:1-12.

11. Vitu E, Bentzur M, Lisowsky T, Kaiser C A, Fass D. Gain of function in an ERV/ALR sulfhydryl oxidase by molecular engineering of the shuttle disulfide. J Mol Biol 2006; 1:89-101.
12. Alon A, Heckler E J, Thorpe C, Fass D. QSOX contains a pseudo-dimer of functional and degenerate sulfhydryl oxidase domains. FEBS Lett 2010; 8:1521-5.
13. Hoober K L, Joneja B, White H B, 3rd, Thorpe C. A sulfhydryl oxidase from chicken egg white. J Biol Chem 1996; 48:30510-6.
14. Hoober K L, Glynn N M, Burnside J, Coppock D L, Thorpe C. Homology between egg white sulfhydryl oxidase and quiescin Q6 defines a new class of flavin-linked sulfhydryl oxidases. J Biol Chem 1999; 45:31759-62.
15. Morel C, Adami P, Musard J, Duval D, Radom J, Jouvenot M. Involvement of sulfhydryl oxidase QSOX1 in the protection of cells against oxidative stress-induced apoptosis. Experimental Cell Research 2007; 19:3971-82.
16. Song H, Zhang B, Watson M A, Humphrey P A, Lim H, Milbrandt J. Loss of Nkx3.1 leads to the activation of discrete downstream target genes during prostate tumorigenesis. Oncogene; 2009. p. 3307-19.
17. Ouyang X, DeWeese T L, Nelson W G, Abate-Shen C. Loss-of-function of Nkx3.1 promotes increased oxidative damage in prostate carcinogenesis. Cancer Research; 2005. p. 6773-9.
18. Bowen C, Bubendorf L, Voeller H J, Slack R, Willi N, Sauter G, et al. Loss of NKX3.1 expression in human prostate cancers correlates with tumor progression. Cancer Res 2000; 21:6111-5.
19. Ouyang H, Mou L, Luk C, Liu N, Karaskova J, Squire J, et al. Immortal human pancreatic duct epithelial cell lines with near normal genotype and phenotype. Am J Pathol 2000; 5:1623-31.
20. Zuo D, Mohr S E, Hu Y, Taycher E, Rolfs A, Kramer J, et al. PlasmID: a centralized repository for plasmid clone information and distribution. Nucleic Acids Res 2007; Database issue:D680-4.
21. Snoek-van Beurden P A M, Von den Hoff J W. Zymographic techniques for the analysis of matrix metalloproteinases and their inhibitors. BioTechniques 2005; 1:73-83.
22. Kessenbrock K, Plaks V, Werb Z. Matrix metalloproteinases: regulators of the tumor microenvironment. Cell 2010; 1:52-67.
23. Koorstra J B, Feldmann G, Habbe N, Maitra A. Morphogenesis of pancreatic cancer: role of pancreatic intraepithelial neoplasia (PanINs). Langenbecks Arch Surg 2008; 4:561-70.
24. Coppock D L, Kopman C, Scandalis S, Gilleran S. Preferential gene expression in quiescent human lung fibroblasts. Cell Growth Differ 1993; 6:483-93.
25. Fass D. The Erv family of sulfhydryl oxidases. Biochim Biophys Acta 2008; 4:557-66.
26. Evan G I, Vousden K H. Proliferation, cell cycle and apoptosis in cancer. Nature 2001; 6835:342-8.
27. Firpo M A, Deer E L, Gonzalez-Hernandez J, Coursen J D, Shea J E, Ngatia J, et al. Phenotype and Genotype of Pancreatic Cancer Cell Lines. Pancreas 2010; 4:425-35.
28. Bloomston M, Zervos E E, Rosemurgy A S. Matrix metalloproteinases and their role in pancreatic cancer: a review of preclinical studies and clinical trials Ann Surg Oncol 2002; 7:668-74.
29. Tian M, Cui Y Z, Song G H, Zong M J, Zhou X Y, Chen Y, et al. Proteomic analysis identifies MMP-9, DJ-1 and A1BG as overexpressed proteins in pancreatic juice from pancreatic ductal adenocarcinoma patients. BMC Cancer 2008241.
30. Pryczynicz A, Guzinska-Ustymowicz K, Dymicka-Piekarska V, Czyzewska J, Kemona A. Expression of matrix metalloproteinase 9 in pancreatic ductal carcinoma is associated with tumor metastasis formation. Folia Histochem Cytobiol 2007; 1:37-40.
31. Kupai K, Szucs G, Cseh S, Hajdu I, Csonka C, Csont T, et al. Matrix metalloproteinase activity assays: Importance of zymography. Journal of Pharmacological and Toxicological Methods 2010; 2:205-9.
32. Wu W S. The signaling mechanism of ROS in tumor progression. Cancer Metast Rev 2006; 4:695-705.
33. Kar S, Subbaram S, Carrico P M, Melendez J A. Redox-control of matrix metalloproteinase-1: a critical link between free radicals, matrix remodeling and degenerative disease. Respir Physiol Neurobiol 2010; 3:299-306.

Example 2

We designed two short hairpin RNAs (shRNA1 and shRHA2) to knock-down QSOX1 protein expression in tumor cells.

shRNA1—Targeting QSOX1 sequence begins at the 970$^{th}$ base pair—

(SEQ ID NO: 17)
ATCTACATGGCTGACCTGGAA shRNA2—Targeting QSOX1 sequence begins at the 1207$^{th}$ base pair—

(SEQ ID NO: 18)
AGGAAAGAGGGTGCCGTTCTT

Figure 6:
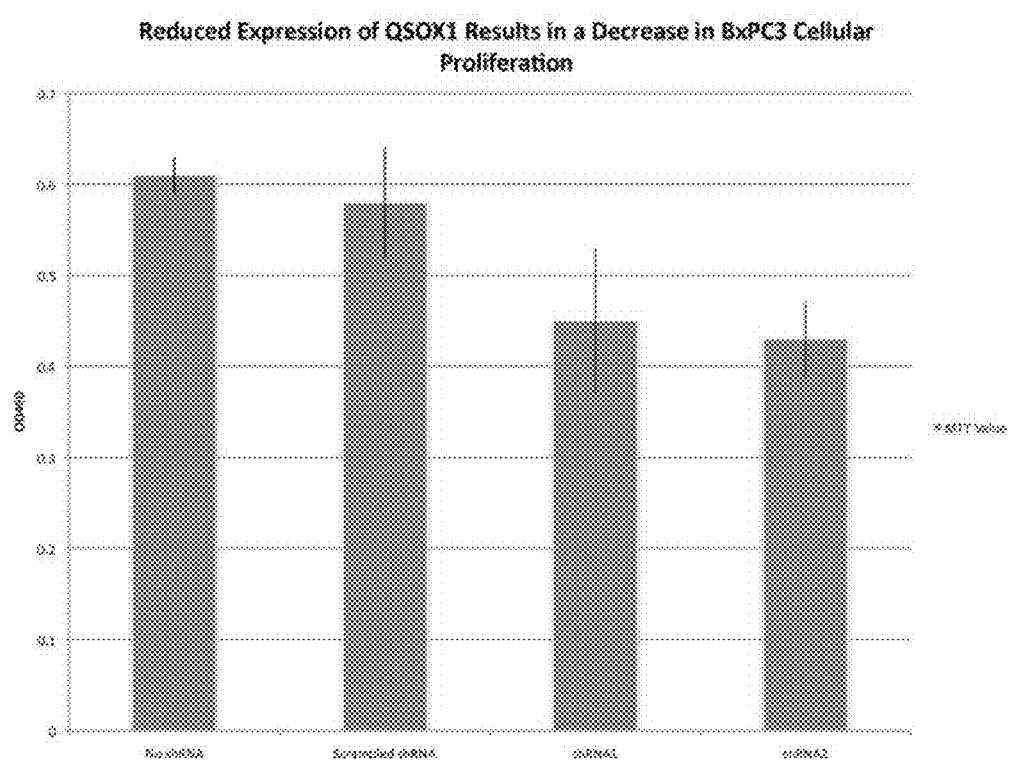
FIG. 6. Cellular proliferation was measured by MTT assay 4 days post-transfection shows that knockdown of QSOX1 short and long form expression by transient lipid-mediated transfection of shRNA results in a decrease in tumor cell viability as measured by a cellular mitochondrial respiration assay (MTT assay). This supports the idea that shRNA or other RNAi species could be used as a drug to suppress QSOX1 protein expression, and inhibit the growth, invasion, and metastases of tumors over-expressing QSOX1. No shRNA—Untreated BxPC3 Cells; Scrambled shRNA—Negative control. BxPC3 cells transfected with scrambled shRNA control vector; shRNA1—BxPC3 cells transfected with shRNA1 for 4 days; shRNA2—BxPC3 cells transfected with shRNA2 for 4 days.
Figure 7:
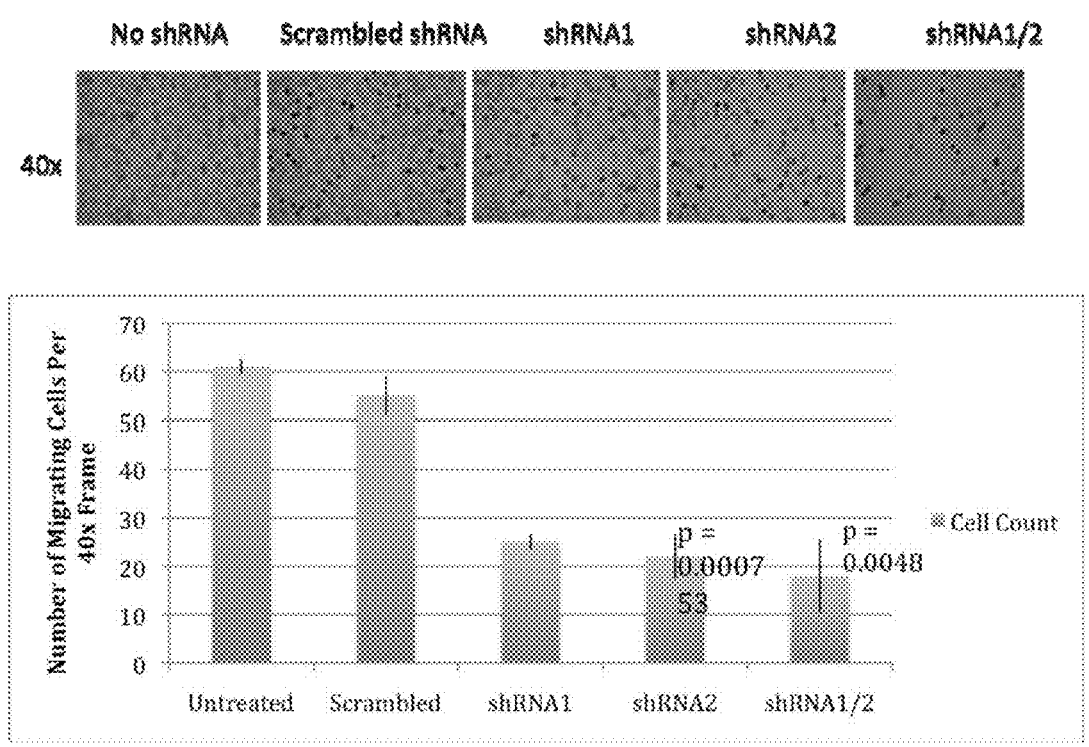
FIG. 7. Invasion Assay shows that by knocking down QSOX1 with the above shRNA we are able to see a decrease in tumor cell invasion. Cells were transfected, allowed to recover for 4 days, resuspended in serum free media and added to 8 um (pore size) microwell inserts coated with Matrigel™. The inserts were placed in cell culture media containing 10% fetal bovine serum such that the bottom half of the outside of the insert was exposed to the media. After 24 hours incubation at 37° C., 5% $CO_2$, the inserts were removed and washed in buffer. Cells that were able to degrade the Matrigel™ coating and invade through the 8 um pores in the insert were counted on the underside of the well. Using the Matrigel™ assay we are able to show that when we knock down QSOX1 in BxPC3 (pancreatic cancer cells) the cells are no longer able to degrade the basement membrane components resulting in a decrease in cellular invasion. Untreated—Untreated BxPC3 Cells; Scrambled—BxPC3 cells transfected with scrambled shRNA control vector. Invasion measured at 4 days post-transfection; shRNA1—BxPC3 cells transfected with shRNA1 and invasion measured 4 days post-transfection; shRNA2—BxPC3 cells transfected with shRNA2 and invasion measured 4 days post-transfection; shRNA1/2—BxPC3 cells transfected with a combined shRNA1 and shRNA2. Cells were measured for invasion properties 4 days post-transfection.

QSOX1 shRNA1 hybridizes with nucleotides 970-989 of the QSOX1 transcript. QSOX1 shRNA2 hybridizes to nucleotides 1207-1226 of the transcript. Both shRNAs, independently and together suppressed the production of QSOX1 protein (data not shown) and cell proliferation. Upon cloning the QSOX1 shRNA into a eukaryotic expression vector (pCS2 mammalian overexpression vector with a CMV promoter) and using it to transfect a pancreatic tumor cell line (BxPC-3), a 30-40% decrease in cell viability was observed, over a 4 to 6 day period, compared to untreated and scrambled shRNA controls. (FIG. 6) Using the same transfection protocol in a separate experiment, we made an additional observation that QSOX1 shRNA-transfected BxPC-3 cells were inhibited from invading through a Matrigel™ basement membrane composed of collagen, laminin and fibronectin approximately 70% when both QSOX1 shRNAs were combined (FIG. 7).

A summary of the data obtained from these studies is shown in the table below:

| Sample | % Decrease in QSOX1 protein expression | Invasion of tumor cells through a basement membrane | Viability/mitochondrial respiration |
| --- | --- | --- | --- |
| shRNA1 | 37 | 63 | 39 |
| shRNA2 | 10 | 69 | 48 |
| shRNA1/2 | 41 | 77 | 50 |

Values in table represent % decreases in protein expression or activity compared to scrambled shRNA in the same CMV driven pCS2 mammalian overexpression vector., Knockdown is transient in this pCS2 vector.

Example 3

Figure 8:
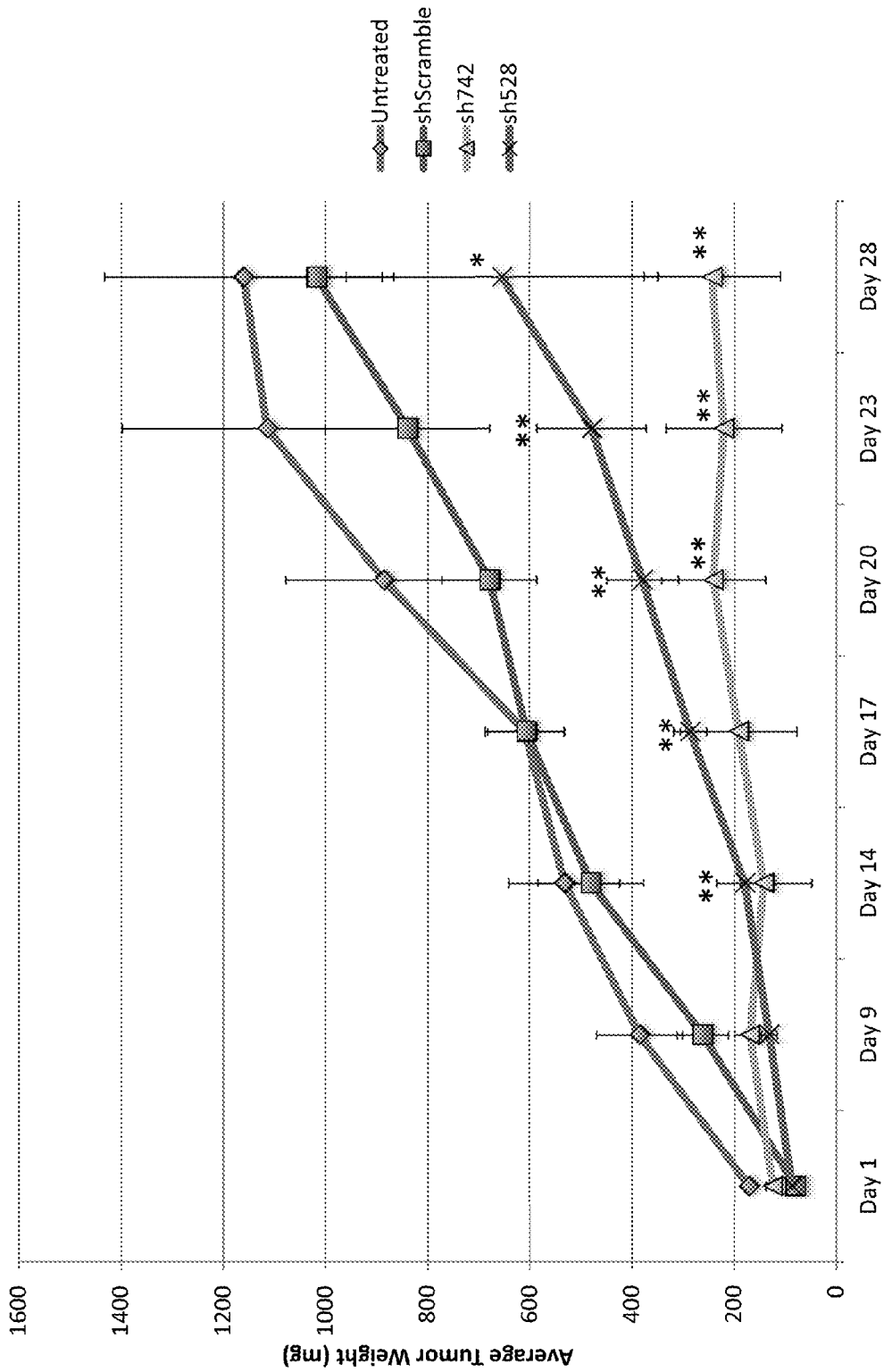
FIG. 8 is a graph showing MIAPaCa2 pancreatic tumor cell xenograft growth rate as a result of shRNA knockdown assays described in Example 3. Human pancreatic tumor cells (MIAPaCa2) were transduced with a lentivirus encoding shQSOX1 (sh528 and sh742) and shScramble (control). One million MIAPaCa2 cells were mixed with Matrigel and used to inoculate nude mice (5 mice/group) on day 0. After day 12, tumor growth was measured every 3 days (x-axis) and reported as "Tumor volume" on the Y-axis. "Untreated" indicates that tumor cells were not transduced.
Figure 9:
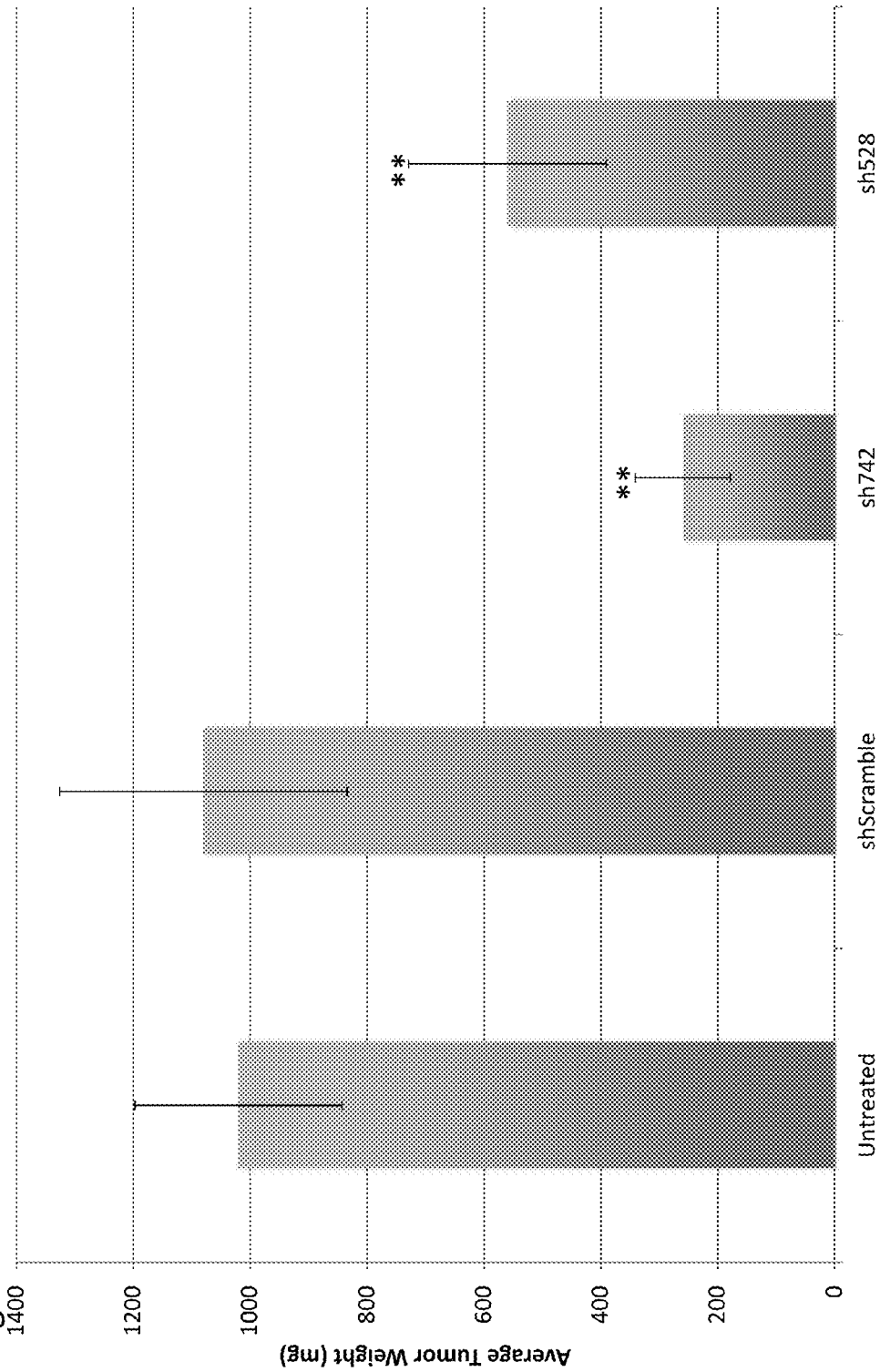
FIG. 9 is a graph showing MIAPaCa3 pancreatic tumor cell xenograft final tumor weights as a result of shRNA knockdown assays described in Example 3.

MIAPaCa2 and Panc-1 pancreatic tumor cells were transduced with shRNA that specifically knocked down QSOX1 protein in the tumor cells. The shRNAs used to knockdown QSOX1 in tumor cells were QSOX1 sh742 (5'-CCGG GCCAATGTGGTGAGAAAGTTTCTCGAGAAACTTT
CTCACCACATTGGCTTTTTG-3' (SEQ ID NO: 26)) and
shRNA QSOX1 sh528 5'-CCGGACAATGAAGAAGC-
CTTT-3' (sense) (SEQ ID NO:21), Nude mice Human pancreatic tumor cells (MIAPaCa2) were transduced with a lentivirus encoding shQSOX1 (sh528 and sh742) and shScramble (control). One million MIAPaCa2 cells were mixed with Matrigel and used to inoculate nude mice (5 mice/group) on day 0. After day 12, tumor growth was measured every 3 days (x-axis) and reported as "Tumor volume" on the Y-axis. "Untreated" indicates that tumor cells were not transduced. (see FIGS. 8 and 9). This in vivo experiment thus validates QSOX1 as a potential target for anti-neoplastic drugs. Any other type of inhibitor of QSOX1 expression or function would have a similar effect on tumor cell growth.

Example 4

In this present study, we evaluated QSOX1 protein expression in breast adenocarcinoma cell lines MCF7, BT474 and BT549 and in a breast tumor tissue microarray. Using short hairpin RNA (shRNA) specific for QSOX1-S and -L, we assessed the effects of QSOX1 knockdown on cell growth, cell cycle, apoptosis, invasion and matrix metalloproteinase activity. The loss of QSOX1 significantly affected tumor cell proliferation and dramatically suppressed tumor cell invasion through matrigel. The addition of exogenous recombinant human QSOX1 (rhQSOX1) rescued the invasive capabilities of MCF7, BT474 and BT549 validating the pro-invasive function of QSOX1. We further report the mechanism of QSOX1-mediated invasion in vitro is due in part, to elevated MMP-9 activity.

Expression of QSOX 1 in Tumor Cells Promotes Cellular Proliferation

To begin to assess the mechanistic role that QSOX1 plays in tumor cells we stably knocked-down QSOX1 expression in MCF7, BT549 and BT474 cells using two lentiviral shRNA constructs, sh742 and sh528 (data not shown). QSOX1 protein expression was assessed following stable knock-down relative to isogenic parental cell lines by western blotting. Densitometry of the QSOX1 protein relative to alpha-tubulin expression indicates that sh742 and sh528 resulted in a knock-down of QSOX1-S expression in MCF7 cells by 85% and 82%, respectively. In BT549 cells the knock-down was 65% and 77%, and for BT474 cells by 40% and 36%, respectively.

The growth rates of shQSOX1-transduced MCF7, BT549 and BT474 cells were then evaluated compared to isogenic controls. An equal number of untransduced (parental), shScramble, sh742 and sh528 cells were seeded in 96 well plates and assayed for proliferation over 5 days using the MTT assay. ShQSOX1-transduced MCF7, BT549 and BT474 cells displayed a decrease in cell growth compared to shScrambled and parental controls. In MCF7 cells, sh742 and sh528 showed a 66% decrease in cell growth, while sh742 and sh528 suppressed growth of BT549 by 78% and 69%, respectively, and sh742 and sh528 suppressed growth of BT474 by 52% and 29%, respectively by day 5. We confirmed our MTT results by performing Trypan blue staining over 5 days using the same incubation conditions as in the MTT assay. These results suggest that QSOX1 helps drive tumor cell growth.

Cell Cycle, Apoptosis and Autophagy Analysis

We hypothesized that a shQSOX1-mediated decrease in cell proliferation could be the result of abnormal regulation of the cell cycle, an increase in apoptosis or the result of autophagosome formation. To address this, propidium iodide (PI) was used in flow cytometry to evaluate the effects of shQSOX1 on cell cycle. In MCF7 cells, both shQSOX1 RNAs showed a slight decrease in $G_1$ and an increase (11-12%) in S phase, while in BT474 cells both shQSOX1 RNAs showed a slight 12% increase in $G_1$ and a 26% decrease in S phase but neither shQSOX1 RNA sequence had any effect in BT549 cells compared to untreated and shScramble controls (data not shown).

Next we determined if the decrease in cellular proliferation was due to an increase in apoptosis or autophagy. To assess apoptosis, we analyzed MCF7 and BT474 transduced cells for Annexin V/PI [18]. We subsequently probed MCF7 and BT549 transduced cells for LC3, a protein that is necessary for auotphagosome formation [19]. If the expression of QSOX1 prevented cellular apoptosis or autophagy we would expect to see an increase in expression of Annexin V and LC3 in shQSOX1 transduced cells, but we did not observe any statistically significant increases in Annexin V positive cells (data not shown). This correlates with our previous results in pancreas cancer that the suppression of QSOX1 does not lead to cell death or autophagy.

Suppression of QSOX1 Expression Inhibits Tumor Cell Invasion

Figure 10:
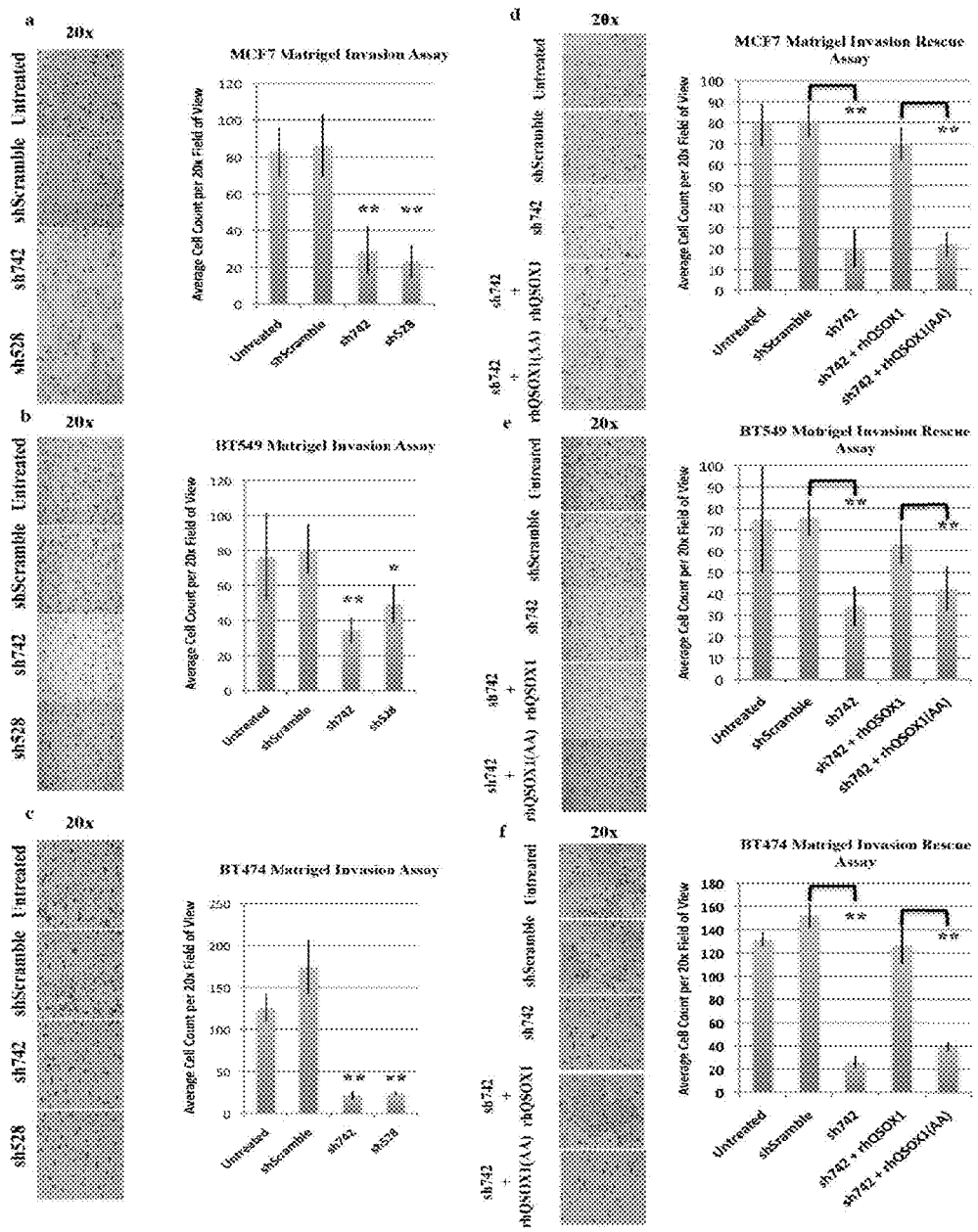
FIG. 10 QSOX1 promotes tumor cell invasion. a.) MCF7, b.) BT549 and c.) BT474 cells transduced with shSramble, sh742 and sh528 shRNAs were seeded at equal densities in the top chamber of Matrigel invasion wells and allowed to incubate for 48 (BT549 and BT474) and 72 (MCF7) hours, after which cells that had digested Matrigel and migrated through the 8 um pores were counted on the underside of the insert. Representative 20× images are presented. MCF7 cells transduced with sh742 and sh528 show a 65% and 71% decrease in invasion. BT549 cells transduced with sh742 and sh528 showed a 60% and 40% decrease in invasion. BT474 cells transduced with sh742 and sh528 show an 82% decrease in invasion. Each knockdown was compared to shScramble controls. The invasive phenotype of shQSOX-transduced MCF7 (d.), BT549 (e.) and BT474 (f.) cells was rescued by exogenous incubation with catalytically active rhQSOX1. rhQSOX1 (AA) mutant is a mutant without enzymatic activity, generously provided by Dr. Debbie Fass. Graphs represent average±SD (MCF7, BT549 and BT474 n=3), significance *, P<0.05, ** P<0.005.

The process of tumor cell invasion involves the degradation of basement membrane (BM) components such as laminin, collagen and fibronectin before a tumor cell is able to invade other tissues [20]. We performed a modified Boyden chamber assay using Matrigel-coated inserts in which tumor cells must degrade the Matrigel and migrate through a membrane with 8 um pores to gain access to nutrient rich media. Sh742 and sh528-transduced MCF-7, BT549 and BT474 tumor cells were added to Matrigel-coated, 8 um pore inserts in serum-free medium. After 72 (MCF7) and 48 (BT549 and BT474) hours of incubation, tumor cells that were able to degrade Matrigel and migrate through 8 um pores onto the underside of the insert were counted (FIGS. 10*a*, *b* and *c*). Our results demonstrate that knockdown of QSOX1 expression in MCF7 leads to a 65% and 71% reduction in invasion of sh742 and sh528 transduced tumor cells, respectively. For BT549 sh742 and sh528-transduced tumor cells, 60% and 40% decreases in invasion through Matrigel were observed. Suppression of QSOX1 expression in BT474 cells leads to an 85% reduction in invasion of both sh742 and sh528 transduced tumor cells. These data suggest that QSOX1 plays a role in regulating invasive behavior in vitro irrespective of breast tumor subtype and hormone receptor status.

To prove that suppression of QSOX1 protein expression was responsible for loss of tumor cell invasion, we performed a rescue experiment in which recombinant human QSOX1 (rhQSOX1, generously provided by Dr. Colin Thorpe) was added to shQSOX1-MCF7, shQSOX1-BT549 and shQSOX1-BT474 cells during the invasion assay. As a control for the enzymatically active QSOX1, a mutant rhQSOX1 in which the CxxC motif in the thioredoxin-1 domain was mutated to AxxA (rhQSOX1 (AA), generously provided by Dr. Debbie Fass) was added to the invasion assay. Addition of enzymatically active rhQSOX1 rescued the invasive phenotype of the shQSOX1-transduced tumor cells (FIG. 10*d-f*), while the addition of the rhQSOX1 (AA) did not rescue invasion of the shQSOX1-transduced tumor cells.

Decrease in QSOX1 Leads to a Decrease in Matrix Metalloproteinase Activity

Since knockdown of QSOX1 resulted in decreased breast tumor cell invasion, it was important to determine a mechanism for how QSOX1 might facilitate invasion. Matrix metalloproteinases (MMP) have been shown to play key roles in breast tumor invasion and metastasis [21]. Both MMP-2 and -9 mRNA and protein levels have been shown to contribute to breast tumor invasion, metastasis and angiogenesis [22]. Since previous work demonstrated that QSOX1-S is secreted into the extracellular matrix where MMPs are activated, we hypothesized that QSOX1 might help activate MMP-2 and -9 proteins. MCF7 and BT549 cells transduced with shScramble, sh742 and sh528 were plated at equal densities and allowed to incubate in serum free media for 48 hours, after which the supernatants were collected and analyzed by gelatin zymography to determine if the loss of QSOX1 leads to a decrease in the functional activity of MMP-2 and -9.

Initial analysis of the results indicates that MCF7 and BT549 possess similar MMP profiles even though it is known that BT549 cells are more invasive. Luminal B like breast tumor cell lines BT474 and ZR75 express do not secrete detectable levels of MMPs [23-25]. However, both MCF7 and BT549 supernatants contain MMP-9 homodimer (130 kDa), a large amount of proteolytically active pro-MMP-9 (92 kDa) with lesser concentrations of proteolytically active pro-MMP-2 (72 kDa).

Figure 11:
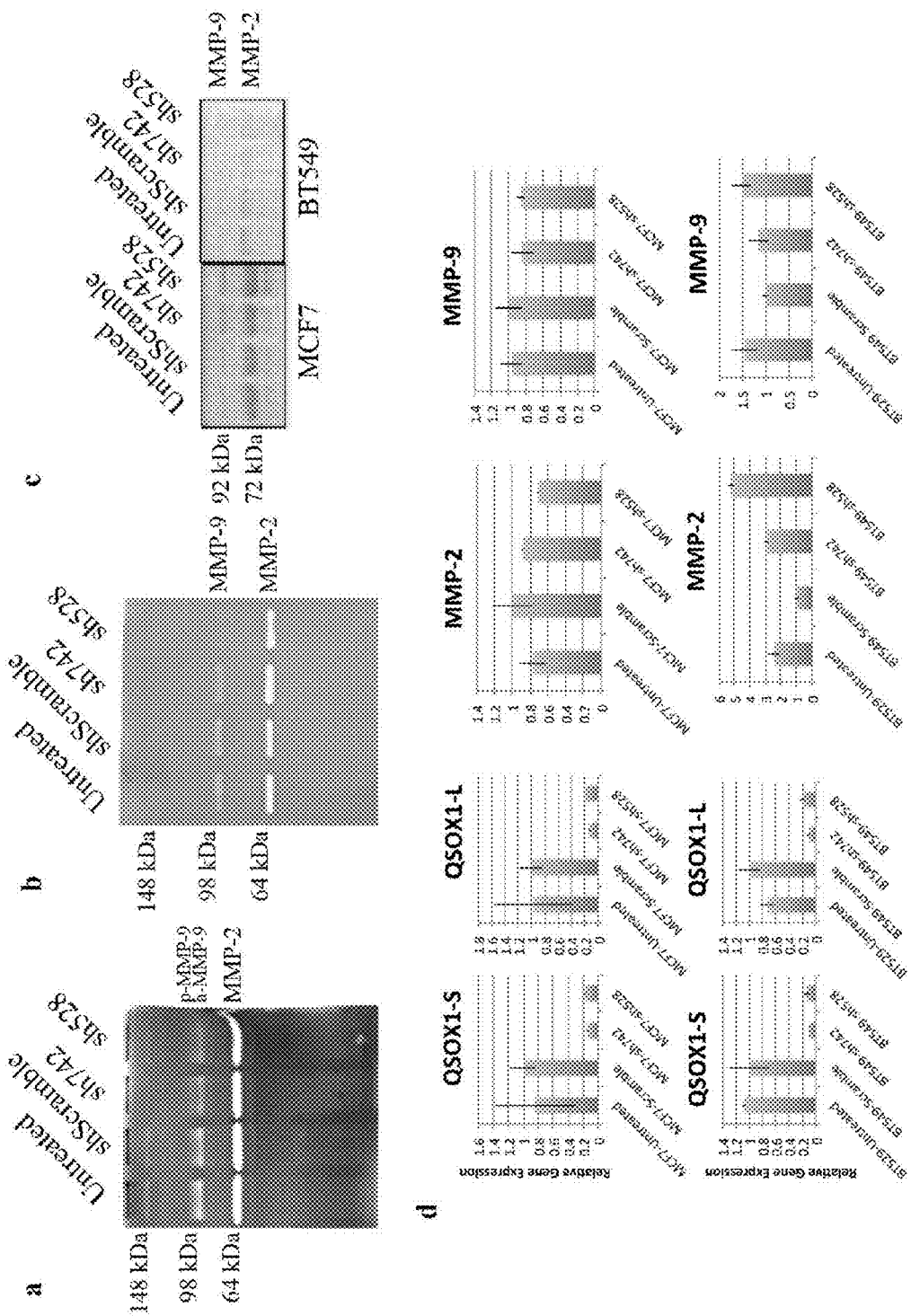
FIG. 11. Reduced expression of QSOX1 in MCF7 and BT549 cells leads to a decrease in functional MMP-9 activity. Gelatin zymography of a) MCF7 and b) BT549 conditioned media shows a decrease in MMP-9 homodimers (130 kDa) and MMP-9 (92 kDa). The percent decrease in MMP-9 expression in MCF7 was: sh742: 70% (p=0.0171); sh528: 77% (p=0.0182), and in BT549 was: sh742: 34% (p=0.0531); sh528: 88% (p=0.0564) compared to shScramble control. c) Western blots of total cell lysate from shRNA treated MCF7 and BT549 probing for MMP-2 and -9 show insignificant changes compared to shScramble control. Full images can be seen in Additional file S3. d) QPCR of QSOX1 transcripts and MMP-2 and -9 transcripts. The graph represents relative gene expression calculated as $\Delta\Delta C_q$ using GAPDH as the endogenous reference gene. MMP-2—MCF7 sh742 (p=0.5294), sh528 (p=0.2112); BT549 sh742 (p=0.0054), sh528 (p=0.0019). MMP-9—MCF7 sh742 (p=0.3981), sh528 (p=0.3385); BT549 sh742 (p=0.4192), sh528 (p=0.0701). Average±SD; significance was determined using a students two-tailed T-Test.

We found that supernatants from MCF7 cells transduced with sh742 and sh528 showed a 70% and 77% decrease, respectively, in pro-MMP9 activity compared to shScramble (FIG. 11$a$). MCF7 supernatants from cells transduced with sh742 and sh528 also showed a 50% and 60% decrease in active MMP-9 (a-MMP-9) as well (FIG. 11$a$). Supernatants from BT549 cells transduced with sh742 and sh528 showed a 34% and 88% decrease, respectively, in MMP-9 (FIG. 11$b$). Decreases in the proteolytic activity of MMP-9, using gelatin as a substrate, provide a mechanism for the shQSOX1-mediated suppression of invasion through Matrigel.

To extend our hypothesis that QSOX1 is activating or modifying MMPs post-translationally, we performed a Western blot on total cell lysate from MCF7 and BT549 transduced cells as well as performed quantitative real time PCR (qPCR) to determine if the loss of QSOX1 affected MMP protein and RNA levels (FIG. 11$c,d$). Our results indicate that the intracellular amount of MMP-2 and -9 protein is similar between the untreated, shScramble, sh742 and sh528 samples in MCF7 and BT549 cells (FIG. 11$c$). FIG. 11$d$ demonstrates that the loss of QSOX1 also has no significant effect on the transcriptional activity of MMP-2 and -9. These results add confidence to our hypothesis that QSOX1 is involved in the post-translational activation of MMPs.

Material and Methods for Example 4
Cell Culture

Breast adenocarcinoma MCF7, MDA-MB-468, MDA-MB-453, BT474, ZR75, BT549 and MDA-MB-231 cancer cell lines were cultured in DMEM with 10% fetal bovine serum (FBS) (Gibco). Immortal human non-tumorigenic breast epithelial cells (MCF10A) were cultured in Clontech KGM-2 karotinocyte media (Gibco). All cell lines were grown at 37° C. with 5% $CO_2$. All cell lines tested negative for mycoplasma contamination using, Venor GeM *Mycoplasma* Detection Kit, (Sigma).

Generation of Short hairpin (sh) RNA and Lentiviruses Production

As described in previous examples.

Generation of shQSOX1-Transduced Tumor Cell Lines

Stable transduction of sh742, sh528, and shScramble into MCF7, BT474 and BT549 cell lines was performed by first seeding the cells at $6 \times 10^5$ cells/well in a 6 well plate and incubating overnight. The next day the cells were transduced by adding 8 ug/mL polybrene (Millipore) and 200 ul sh742, sh528, and shScramble lentivirus produced from 293T cells to each well. The cells were then incubated for 24 hours. The following day fresh DMEM with 10% FBS was added, containing 1 ug/mL puromycin (Sigma) to select for the transduced cells. QSOX1 knockdown was measured by western blot.

SDS-PAGE-Western Blotting

Western blotting was performed using cell lysates from MCF10A, MCF7, MDA-MB-468, MDA-MB-453, BT474, ZR 75, BT549 and MDA-MB-231. Cell lysates were generated by harvesting $2.5 \times 10^6$ cells by centrifugation followed by lysis using RIPA buffer (50 mM Tris-HCl, pH 7.4, 150 mM NaCl, 1 mM EDTA, and 1% Triton X-100) with 1× Sigma-FAST Protease Inhibitor Cocktail Tablet, EDTA Free. Protein in the cell lysate was measured using the micro BCA protein assay kit (Thermo Scientific). All samples were then normalized to 2 mg/mL (20 ug total protein per lane). Samples were run on 10% SDS-polyacrylamide gels then transferred onto Immun-Blot™ PVDF Membranes (Bio-Rad). Rabbit polyclonal anti-QSOX1 (ProteinTech), rabbit polyclonal anti-alpha-tubulin (Cell Signaling), rabbit polyclonal anti-MMP-2 and -9 (Sigma), mouse monoclonal caspase 3 (Cell Signalling), and rabbit polyclonal LC3 (Cell Signalling) antibodies were diluted according to the manufacturers' instructions and as determined in preliminary experiments, in 1% BSA in 1×TBS+0.01% Tween-20 and incubated overnight. Goat anti-rabbit or anti-mouse IgG-alkaline phospatase or HRP secondary antibody was used at a 1:5000 dilution and incubated with the blot for 1 h followed by washing. BCIP/NBT substrate (Pierce Chemical, Rockford, Ill.) was added and the blot was developed at room temperature (RT) for approximately 10 minutes for alkaline phosphatase secondary antibody. For samples incubated in goat anti-rabbit or mouse HRP secondary the blots were developed using Novex ECL Chemiluminescent Substrate Reagent Kit. Quantification of band intensity was measured using Image J and is presented as percent change from the scrambled shRNA control. Full gel images are available in the Additional file 1. All gel images were annotated and processed using Photoshop CS3.

MTT (3-(4,5-Dimethylthiazol-2-yl)-2,5-diphenyltetrazolium bromide) Assay

Cells were seeded at $3 \times 10^3$ cell/well in a 96-well plate in triplicate, and incubated at 37° C., 5% $CO_2$ over the course of 5 days. The MTT assay was performed over a 5 day period according to the manufacturer's instructions (Invitrogen-Molecular Probes, Vybrant MTT Cell Proliferation Assay Kit). Results are presented as mean+/−S.D. Student's two tailed T-test was performed to determine significance.

Trypan Blue Live/Dead Cell Growth Assay

Cells were seeded at $2.5 \times 10^4$ cells/well in a 12-well plate in triplicate, and incubated at 37° C., 5% $CO_2$ over the course of 5 days. The cells were removed with Cell Stripper, pelleted and brought back up in 1 mL PBS. A 30 ul aliquot was then used to determine total cell number. The cells were stained at a 1:1 ratio with 0.1% Trypan Blue and are reported as total number of live cells.

RNA Isolation and cDNA Synthesis

Total RNA isolation was performed according to the manufacturer's instructions for animal cells using spin technology (RNeasy Mini Kit, Qiagen). After RNA was isolated from each sample was reverse transcribed with qScript cDNA Sythesis Kit, Quanta Biosciences according to the manufacturer's instructions.

Boyden Chamber and Invasion Recovery Assay

Invasion assays were performed using BD BioCoat™ BD Matrigel™ and non-Matrigel™ control Invasion chambers with 8.0 μm pore size polyethylene terephthalate (PET) membrane inserts in 24-well format. The assay was performed according to the manufacturer's instructions (BD Bioscience). $4 \times 10^4$ cells/well were seeded into the inner matrigel chamber in serum free DMEM. The outer chamber contained 10% FBS in DMEM. MCF7, BT474 and BT549 cells were incubated for 72, 48 and 48 hours, respectively at 37° C., 5% $CO_2$. For invasion rescue assays MCF7, BT474 and BT549 cells were incubated with 50 nM rQSOX1 as well as catalytically inactive mutant rQSOX1 (rQSOX1-AA). Cells that invaded through the Matrigel and migrated through the pores onto the bottom of the insert were fixed in 100% methanol and then stained in hematoxylin (Invitrogen). The total number of invading cells were determined by counting the cells on the underside of the insert from triplicate wells (6 fields per insert) at 20× magnification. The extent of invasion was expressed as the mean+/−S.D. Significance was determined using the Student's two-tailed T-test. Results presented are from one of three independent experiments.

Gelatin Zymography

The identification of MMP was performed using gelatin zymography. Zymography experiments were performed essentially as previously described by Katchman et al. Minor changes in the protocol are the inclusion of untreated MCF7 and BT549 cells as well as short hairpin-transduced cells were seeded at $5×10^5$ cells/well (12 well plates) in DMEM with 10% FBS. The next day, cells were then washed with 1×PBS and the media was changed to serum-free DMEM and incubated for 48 hours instead of 24 hours before being collected and protein concentrations determined using a BCA assay. Quantification of band intensity was measured using Image J and is presented as percent change from the scrambled shRNA control.

References for Example 4

[1] D. C. Sgroi, Preinvasive Breast Cancer, Annu Rev. Pathol. Mech. Dis, 5 (2010) 193-221.

[2] A.C. Society, Cancer Facts and Figures 2012, Atlanta: American Cancer Society, (2012) 1-68.

[3] R. Siegel, D. Naishadham, A. Jemal, Cancer statistics, 2012, CA: a Cancer Journal for Clinicians, 62 (2012) 10-29.

[4] K. Antwi, G. Hostetter, M. J. Demeure, B. A. Katchman, G. A. Decker, Y. Ruiz, T. D. Sielaff, L. J. Koep, D. F. Lake, Analysis of the plasma peptidome from pancreas cancer patients connects a peptide in plasma to overexpression of the parent protein in tumors, J. Proteome Res, 8 (2009) 4722-4731.

[5] B. A. Katchman, K. Antwi, G. Hostetter, M. J. Demeure, A. Watanabe, G. A. Decker, L. J. Miller, D. D. Von Hoff, D. F. Lake, Quiescin Sulfhydryl Oxidase 1 Promotes Invasion of Pancreatic Tumor Cells Mediated by Matrix Metalloproteinases, Molecular Cancer Research, 9 (2011) 1621-1631.

[6] D. L. Coppock, C. Thorpe, Multidomain Flavin-Dependent Sulfhydryl Oxidases, Antioxid. Redox Signal, 8 (2006) 300-311.

[7] E. J. Heckler, A. Alon, D. Fass, C. Thorpe, Human Quiescin-Sulfhydryl Oxidase, QSOX1: Probing Internal Redox Steps by Mutagenesist, Biochemistry, 47 (2008) 4955-4963.

[8] A. Alon, E. J. Heckler, C. Thorpe, D. Fass, QSOX contains a pseudo-dimer of functional and degenerate sulfhydryl oxidase domains, FEBS Lett, 584 (2010) 1521-1525.

[9] D. L. Coppock, C. Thorpe, Multidomain flavin-dependent sulfhydryl oxidases, Antioxid. Redox Signal, 8 (2006) 300-311.

[10] A. Alon, I. Grossman, Y. Gat, V. K. Kodali, F. DiMaio, T. Mehlman, G. Haran, D. Baker, C. Thorpe, D. Fass, The dynamic disulphide relay of quiescin sulphydryl oxidase, Nature, 488 (2012) 414-418.

[11] E. J. Heckler, P. C. Rancy, V. K. Kodali, C. Thorpe, Generating disulfides with the Quiescin-sulfhydryl oxidases, Biochimica Et Biophysica Acta (BBA)-Molecular Cell Research, 1783 (2008) 567-577.

[12] H. Song, B. Zhang, M. A. Watson, P. A. Humphrey, H. Lim, J. Milbrandt, Loss of Nkx31 leads to the activation of discrete downstream target genes during prostate tumorigenesis, Oncogene, 28 (2009) 3307-3319.

[13] K. Antwi, G. Hostetter, M. J. Demeure, B. A. Katchman, G. A. Decker, Y. Ruiz, T. D. Sielaff, L. J. Koep, D. F. Lake, Analysis of the plasma peptidome from pancreas cancer patients connects a peptide in plasma to overexpression of the parent protein in tumors, J. Proteome Res, 8 (2009) 4722-4731.

[14] M. Ringnér, E. Fredlund, J. Häkkinen, Å. Borg, J. Staaf, GOBO: Gene Expression-Based Outcome for Breast Cancer Online, PLoS ONE, 6 (2011) e17911.

[15] T. Sørlie, C. M. Perou, R. Tibshirani, T. Aas, S. Geisler, H. Johnsen, T. Hastie, M. B. Eisen, M. Van De Rijn, S. S. Jeffrey, Gene expression patterns of breast carcinomas distinguish tumor subclasses with clinical implications, Proc. Natl. Acad. Sci. U.S.a, 98 (2001) 10869.

[16] T. Blick, E. Widodo, H. Hugo, M. Waltham, M. E. Lenburg, R. M. Neve, E. W. Thompson, Epithelial mesenchymal transition traits in human breast cancer cell lines, Clin Exp Metastasis, 25 (2008) 629-642.

[17] C. Morel, P. Adami, J.-F. Musard, D. Duval, J. Radom, M. Jouvenot, Involvement of sulfhydryl oxidase QSOX1 in the protection of cells against oxidative stress-induced apoptosis, Exp. Cell Res, 313 (2007) 3971-3982.

[18] J. Plati, O. Bucur, R. Khosravi-Far, Apoptotic cell signaling in cancer progression and therapy, Integr. Biol, 3 (2011) 279.

[19] Y. Chen, D. J. Klionsky, The regulation of autophagy—unanswered questions, Journal of Cell Science, 124 (2010) 161-170.

[20] M. Bacac, I. Stamenkovic, Metastatic Cancer Cell, Annu Rev. Pathol. Mech. Dis, 3 (2008) 221-247.

[21] E. S. Radisky, D. C. Radisky, Matrix Metalloproteinase-Induced Epithelial-Mesenchymal Transition in Breast Cancer, J Mammary Gland Biol Neoplasia, 15 (2010) 201-212.

[22] E. S. Radisky, D. C. Radisky, Matrix Metalloproteinase-Induced Epithelial-Mesenchymal Transition in Breast Cancer, J Mammary Gland Biol Neoplasia, 15 (2010) 201-212.

[23] P. A. Lambert, K. D. Somers, E. C. Kohn, R. R. Perry, Antiproliferative and antiinvasive effects of carboxyamido-triazole on breast cancer cell lines, Surgery, 122 (1997) 372-379.

[24] M. M. Caffarel, C. Andradas, E. Mira, E. Pérez-Gómez, C. Cerutti, G. Moreno-Bueno, J. M. Flores, I. García-Real, J. Palacios, S. Mañes, M. Guzmán, C. Sánchez, Cannabinoids reduce ErbB2-driven breast cancer progression through Aid inhibition, Mol. Cancer, 9 (2010) 196.

[25] A. Köhrmann, U. Kammerer, M. Kapp, J. Dietl, J. Anacker, Expression of matrix metalloproteinases (MMPs) in primary human breast cancer and breast cancer cell lines: New findings and review of the literature, BMC Cancer, 9 (2009) 188.

[26] B. A. Katchman, K. Antwi, G. Hostetter, M. J. Demeure, A. Watanabe, G. A. Decker, L. J. Miller, D. D. Von Hoff, D. F. Lake, Quiescin Sulfhydryl Oxidase 1 Promotes Invasion of Pancreatic Tumor Cells Mediated by Matrix Metalloproteinases, Molecular Cancer Research, (2011).

[27] D. Hanahan, R. A. Weinberg, Hallmarks of cancer: the next generation, Cell, 144 (2011) 646-674.

[28] T. Blick, E. Widodo, H. Hugo, M. Waltham, M. E. Lenburg, R. M. Neve, E. W. Thompson, Epithelial mesenchymal transition traits in human breast cancer cell lines, Clin Exp Metastasis, 25 (2008) 629-642.

[29] K. B. Yin, N. Miswan, P. Balaram, K. Nadarajan, E. Elstner, Modification of MCF-10A Cells with Pioglitazone and Serum-Rich Growth Medium Increases Soluble Factors in the Conditioned Medium, Likely Reducing BT-474 Cell Growth, Ijms, 13 (2012) 5607-5627.

[30] K. J. Martin, D. R. Patrick, M. J. Bissell, M. V. Fournier, Prognostic Breast Cancer Signature Identified from 3D Culture Model Accurately Predicts Clinical Outcome across Independent Datasets, PLoS ONE, 3 (2008) e2994.

[31] A. Rizki, V. M. Weaver, S. Y. Lee, G. I. Rozenberg, K. Chin, C. A. Myers, J. L. Bascom, J. D. Mott, J. R. Semeiks, L. R. Grate, I. S. Mian, A. D. Borowsky, R. A. Jensen, M. O. Idowu, F. Chen, D. J. Chen, O. W. Petersen, J. W. Gray, M. J. Bissell, A Human Breast Cell Model of Preinvasive to Invasive Transition, Cancer Research, 68 (2008) 1378-1387.

[32] K. Polyak, Heterogeneity in breast cancer, J. Clin. Invest, 121 (2011) 3786-3788.

[33] F. Michor, K. Polyak, The Origins and Implications of Intratumor Heterogeneity, Cancer Prevention Research, 3 (2010) 1361-1364.

[34] M. Hu, K. Polyak, Molecular characterisation of the tumour microenvironment in breast cancer, European Journal of Cancer, 44 (2008) 2760-2765.

[35] B. Bauvois, New facets of matrix metalloproteinases MMP-2 and MMP-9 as cell surface transducers: Outside-in signaling and relationship to tumor progression, BBA—Reviews on Cancer, 1825 (2011) 29-36.

[36] K. Kessenbrock, V. Plaks, Z. Werb, Matrix Metalloproteinases: Regulators of the Tumor Microenvironment, Cell, 141 (2010) 52-67.

[37] Q. Jin, L. X. Yuan, D. Boulbes, J. M. Baek, Y. N. Wang, D. Gomez-Cabello, D. H. Hawke, S. C. Yeung, M. H. Lee, G. N. Hortobagyi, M. C. Hung, F. J. Esteva, Fatty acid synthase phosphorylation: a novel therapeutic target in HER2-overexpressing breast cancer cells, Breast Cancer Research, 12 (2010) R96.

[38] C. R. Andrade, B. S. Stolf, V. Debbas, D. S. Rosa, J. Kalil, V. Coelho, F. R. M. Laurindo, Quiescin sulfhydryl oxidase (QSOX) is expressed in the human atheroma core: possible role in apoptosis, In Vitro Cell. Dev. Biol.—Animal, 47 (2011) 716-727.

We claim:

1. An isolated nucleic acid encoding a shRNA molecule comprising a nucleic acid of 5'-CCGGACAATGAA-GAAGCCTTT-3' (SEQ ID NO: 21) and its complement, or an RNA equivalent thereof; or a nucleic acid of 5'-TCTAGCCA-CAACAGGGTCAAT-3' (SEQ ID NO: 22) and its complement, or an RNA equivalent thereof.

2. An isolated nucleic acid encoding an shRNA molecule comprising a nucleic acid that encodes the complement of a nucleic acid of the general formula:

(SEQ ID NO: 23)
CCGG-X1-CTCGAGAAACTTTCTCACCACATTGGCTTTTG-3' or an RNA equivalent thereof;

wherein X1 is a nucleic acid sequence selected from the group consisting of (SEQ ID NO: 11)
5'-A(T/U)C(T/U)ACA(T/U)GGC(T/U)GACC(T/U)GGAA-3'

(SEQ ID NO: 12)
5'-AGGAAAGAGGG(T/U)GCCG(T/U)(T/U)C(T/U)(T/U)-3', (SEQ ID NO: 13)
5'-GCCAA(T/U)G(T/U)GG(T/U)GAGAAAG(T/U)(T/U)(T/U)-3', (SEQ ID NO: 14)
5'-GCCAAGAAGG(T/U)GAAC(T/U)GGA(T/U)(T/U)-3'.

(SEQ ID NO: 15)
5'-CCGGACAA(T/U)GAAGAAGCC(T/U)(T/U)(T/U)-3'

(SEQ ID NO: 16)
5'-(T/U)C(T/U)AGCCACAACAGGG(T/U)CAA(T/U)-3'

(SEQ ID NO: 17)
5'-ATCTACATGGCTGACCTGGAA-3',

-continued

```
                                            (SEQ ID NO: 18)
5'-AGGAAAGAGGGTGCCGTTCTT-3', (SEQ ID NO: 19)
5'-GCCAATGTGGTGAGAAAGTTT-3', (SEQ ID NO: 20)
5'-GCCAAGAAGGTGAACTGGATT-3', (SEQ ID NO: 21)
5'-CCGGACAATGAAGAAGCCTTT-3';
and (SEQ ID NO: 22)
5'-TCTAGCCACAACAGGGTCAAT-3'.
```

3. A recombinant expression vector comprising the isolated nucleic acid of claim 1 operatively linked to a promoter.

4. The recombinant expression vector of claim 3, wherein the vector comprises a viral vector.

5. A recombinant host cell comprising the recombinant expression vector of claim 3.

6. A pharmaceutical composition, comprising
(a) the isolated nucleic acid of claim 1; and
(b) a pharmaceutically acceptable carrier.

7. A pharmaceutical composition, comprising
(a) the recombinant expression vector of claim 3; and
(b) a pharmaceutically acceptable carrier.

8. A pharmaceutical composition, comprising
(a) the recombinant host cell of claim 5; and
(b) a pharmaceutically acceptable carrier.

9. A recombinant expression vector comprising the isolated nucleic acid of claim 2 operatively linked to a promoter.

10. The recombinant expression vector of claim 9, wherein the vector comprises a viral vector.

11. A recombinant host cell comprising the recombinant expression vector of claim 10.

12. A pharmaceutical composition, comprising
(a) the recombinant expression vector of claim 9; and
(b) a pharmaceutically acceptable carrier.

13. A pharmaceutical composition, comprising
(a) the recombinant host cell of claim 11; and
(b) a pharmaceutically acceptable carrier.

14. A method for tumor treatment, comprising administering to a subject having a tumor an amount effective of an inhibitor of quiescin sulfhydryl oxidase 1 (QSOX1) expression and/or activity, or a pharmaceutically acceptable salt thereof, to treat the tumor, wherein the inhibitor comprises the nucleic acid of claim 1.

15. The method of claim 14, wherein the tumor is a tumor that over-expresses QSOX1 compared to control.

16. The method of claim 14, wherein the subject is one from which tumor-derived QSOX1 peptides can be obtained.

17. The method of claim 16, wherein the tumor-derived QSOX1 peptides are selected from the group consisting of

```
                                            (SEQ ID NO: 3)
NEQEQPLGQWHLS, (SEQ ID NO: 4)
NEQEQPLGQWH, (SEQ ID NO: 5)
EQPLGQWHLS, (SEQ ID NO: 6)
AAPGQEPPEHMAELQR, (SEQ ID NO: 7)
AAPGQEPPEHMAELQ, (SEQ ID NO: 8)
AAPGQEPPEHMAELQRNEQEQPLGQWHLS, (SEQ ID NO: 9)
NEQEQPL,
and (SEQ ID NO: 10)
GQWHLS.
```

18. The method of claim 16 wherein the tumor-derived QSOX1 peptides are obtained from a tissue sample selected from the group consisting of plasma, serum, urine, saliva, and tumor tissue.

19. The method of claim 14, wherein the tumor is a pancreatic tumor.

20. The method of claim 19, wherein the pancreatic tumor comprises a pancreatic adenocarcinoma.

21. A method for tumor treatment, comprising administering to a subject having a tumor an amount effective of an inhibitor of quiescin sulfhydryl oxidase 1 (QSOX1) expression and/or activity, or a pharmaceutically acceptable salt thereof, to treat the tumor, wherein the inhibitor comprises the nucleic acid of claim 2.

22. The method of claim 14, wherein the nucleic acid inhibitor is administered to the subject in a viral vector.

23. The method of claim 22, wherein the tumor is a tumor that over-expresses QSOX1 compared to control.

24. The method of claim 22, wherein the subject is one from which tumor-derived QSOX1 peptides can be obtained.

25. The method of claim 24, wherein the tumor-derived QSOX1 peptides are selected from the group consisting of

```
                                            (SEQ ID NO: 3)
NEQEQPLGQWHLS, (SEQ ID NO: 4)
NEQEQPLGQWH, (SEQ ID NO: 5)
EQPLGQWHLS, (SEQ ID NO: 6)
AAPGQEPPEHMAELQR, (SEQ ID NO: 7)
AAPGQEPPEHMAELQ, (SEQ ID NO: 8)
AAPGQEPPEHMAELQRNEQEQPLGQWHLS, (SEQ ID NO: 9)
NEQEQPL,
and (SEQ ID NO: 10)
GQWHLS.
```

26. The method of claim 24 wherein the tumor-derived QSOX1 peptides are obtained from a tissue sample selected from the group consisting of plasma, serum, urine, saliva, and tumor tissue.

27. The method of claim 22, wherein the tumor is a pancreatic tumor.

28. The method of claim 27, wherein the pancreatic tumor comprises a pancreatic adenocarcinoma.

* * * * *

SEQUENCE LISTING

<160> NUMBER OF SEQ ID NOS: 41

<210> SEQ ID NO 1
<211> LENGTH: 1815
<212> TYPE: DNA
<213> ORGANISM: Homo sapiens

<400> SEQUENCE: 1

```
atgaggaggt gcaacagcgg ctccgggccg ccgccgtcgc tgctgctgct gctgctgtgg      60
ctgctcgcgg ttcccggcgc taacgcggcc ccgcggtcgg cgctctattc gccttccgac     120
ccgctgacgc tgctgcaggc ggacacggtg cgcggcgcgg tgctgggctc ccgcagcgcc     180
tgggccgtgg agttcttcgc ctcctggtgc ggccactgca tcgccttcgc cccgacgtgg     240
aaggcgctgg ccgaagacgt caaagcctgg aggccggccc tgtatctcgc cgccctggac     300
tgtgctgagg agaccaacag tgcagtctgc agagacttca acatccctgg cttcccgact     360
gtgaggttct tcaaggcctt taccaagaac ggctcgggag cagtatttcc agtggctggt     420
gctgacgtgc agacactgcg ggagaggctc attgacgccc tggagtccca tcatgacacg     480 tggccccag  cctgtcccc  actggagcct gccaagctgg aggagattga tggattcttt     540
gcgagaaata acgaagagta cctggctctg atctttgaaa agggaggctc ctacctgggt     600
agagaggtgg ctctggacct gtcccagcac aaaggcgtgg cggtgcgcag ggtgctgaac     660
acagaggcca atgtggtgag aaagtttggt gtcaccgact tcccctcttg ctacctgctg     720
ttccggaatg gctctgtctc ccgagtcccc gtgctcatgg aatccaggtc cttctatacc     780
gcttacctgc agagactctc tgggctcacc agggaggctg cccagaccac agttgcacca     840
accactgcta acaagatagc tcccactgtt tggaaattgg cagatcgctc caagatctac     900
atggctgacc tggaatctgc actgcactac atcctgcgga tagaagtggg caggttcccg     960
gtcctggaag ggcagcgcct ggtggccctg aaaaagtttg tggcagtgct ggccaagtat    1020
ttccctggcc ggcccttagt ccagaacttc ctgcactccg tgaatgaatg gctcaagagg    1080
cagaagagaa ataaaattcc ctacagtttc tttaaaactg ccctggacga caggaaagag    1140
```

| | |
|---|---|
| ggtgccgttc ttgccaagaa ggtgaactgg attggctgcc aggggagtga gccgcatttc | 1200 |
| cggggctttc cctgctccct gtgggtcctc ttccacttct tgactgtgca ggcagctcgg | 1260 |
| caaaatgtag accactcaca ggaagcagcc aaggccaagg aggtcctccc agccatccga | 1320 |
| ggctacgtgc actacttctt cggctgccga gactgcgcta gccacttcga gcagatggct | 1380 |
| gctgcctcca tgcaccgggt ggggagtccc aacgccgctg tcctctggct ctggtctagc | 1440 |
| cacaacaggg tcaatgctcg ccttgcaggt gcccccagcg aggaccccca gttccccaag | 1500 |
| gtgcagtggc caccccgtga actttgttct gcctgccaca atgaacgcct ggatgtgccc | 1560 |
| gtgtgggacg tggaagccac cctcaacttc ctcaaggccc acttctcccc aagcaacatc | 1620 |
| atcctggact ccctgcagc tgggtcagct gcccggaggg atgtgcagaa tgtggcagcc | 1680 |
| gccccagagc tggcgatggg agccctggag ctggaaagcc ggaattcaac tctggaccct | 1740 |
| gggaagcctg agatgatgaa gtcccccaca aacaccaccc cacatgtgcc ggctgaggga | 1800 |
| cctgagctta tttga | 1815 |

<210> SEQ ID NO 2
<211> LENGTH: 2244
<212> TYPE: DNA
<213> ORGANISM: Homo sapiens

<400> SEQUENCE: 2

| | |
|---|---|
| atgaggaggt gcaacagcgg ctccgggccg ccgccgtcgc tgctgctgct gctgctgtgg | 60 |
| ctgctcgcgg ttcccggcgc taacgcggcc ccgcggtcgg cgctctattc gccttccgac | 120 |
| ccgctgacgc tgctgcaggc ggacacggtg cgcggcgcgg tgctgggctc ccgcagcgcc | 180 |
| tgggccgtgg agttcttcgc ctcctggtgc ggccactgca tcgccttcgc ccgacgtgg | 240 |
| aaggcgctgg ccgaagacgt caaagcctgg aggccggccc tgtatctcgc cgccctggac | 300 |
| tgtgctgagg agaccaacag tgcagtctgc agagacttca acatccctgg cttcccgact | 360 |
| gtgaggttct tcaaggcctt taccaagaac ggctcgggag cagtatttcc agtggctggt | 420 |
| gctgacgtgc agacactgcg ggagaggctc attgacgccc tggagtccca tcatgacacg | 480 |
| tggccccag cctgtccccc actggagcct gccaagctgg aggagattga tggattcttt | 540 |
| gcgagaaata cgaagagta cctggctctg atctttgaaa agggaggctc ctacctgggt | 600 |
| agagaggtgg ctctggacct gtcccagcac aaaggcgtgg cggtgcgcag ggtgctgaac | 660 |
| acagaggcca atgtggtgag aaagtttggt gtcaccgact tccccctctt ctacctgctg | 720 |
| ttccggaatg gctctgtctc ccgagtcccc gtgctcatgg aatccaggtc cttctatacc | 780 |
| gcttacctgc agagactctc tgggctcacc agggaggctg cccagaccac agttgcacca | 840 |
| accactgcta caagatagc tcccactgtt tggaaattgg cagatcgctc caagatctac | 900 |
| atggctgacc tggaatctgc actgcactac atcctgcgga tagaagtggg caggttcccg | 960 |
| gtcctggaag gcagcgcct ggtggccctg aaaaagtttg tggcagtgct ggccaagtat | 1020 |
| ttccctggcc ggcccttagt ccagaacttc ctgcactccg tgaatgaatg gctcaagagg | 1080 |
| cagaagagaa ataaaattcc ctacagtttc tttaaaactg ccctggacga caggaaagag | 1140 |
| ggtgccgttc ttgccaagaa ggtgaactgg attggctgcc aggggagtga gccgcatttc | 1200 |
| cggggctttc cctgctccct gtgggtcctc ttccacttct tgactgtgca ggcagctcgg | 1260 |
| caaaatgtag accactcaca ggaagcagcc aaggccaagg aggtcctccc agccatccga | 1320 |
| ggctacgtgc actacttctt cggctgccga gactgcgcta gccacttcga gcagatggct | 1380 |

```
gctgcctcca tgcaccgggt ggggagtccc aacgccgctg tcctctggct ctggtctagc    1440
cacaacaggg tcaatgctcg ccttgcaggt gcccccagcg aggaccccca gttccccaag    1500
gtgcagtggc caccccgtga actttgttct gcctgccaca atgaacgcct ggatgtgccc    1560
gtgtgggacg tggaagccac cctcaacttc ctcaaggccc acttctcccc aagcaacatc    1620
atcctggact ccctgcagc tgggtcagct gcccggaggg atgtgcagaa tgtggcagcc    1680
gccccagagc tggcgatggg agccctggag ctggaaagcc ggaattcaac tctgacccct    1740
gggaagcctg agatgatgaa gtcccccaca aacaccaccc cacatgtgcc ggctgaggga    1800
cctgaggcaa gtcgaccccc gaagctgcac cctggcctca gagctgcacc aggccaggag    1860
cctcctgagc acatggcaga gcttcagagg aatgagcagg agcagccgct ggggcagtgg    1920
cacttgagca gcgagacac aggggctgca ttgctggctg agtccagggc tgagaagaac    1980
cgcctctggg gccctttgga ggtcaggcgc gtgggccgca gctccaagca gctggtcgac    2040
atccctgagg ccagctgga ggcccgagct ggacggggcc gaggccagtg gctgcaggtg    2100
ctgggagggg gcttctctta cctggacatc agcctctgtg tggggctcta ttccctgtcc    2160
ttcatgggcc tgctggccat gtacacctac ttccaggcca agataagggc cctgaagggc    2220
catgctggcc accctgcagc ctga                                          2244
```

<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Asn Glu Gln Glu Gln Pro Leu Gly Gln Trp His Leu Ser
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Asn Glu Gln Glu Gln Pro Leu Gly Gln Trp His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Glu Gln Pro Leu Gly Gln Trp His Leu Ser
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Synthetic

<400> SEQUENCE: 6

```
Ala Ala Pro Gly Gln Glu Pro Pro Glu His Met Ala Glu Leu Gln Arg
1               5                   10                  15
```

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

```
Ala Ala Pro Gly Gln Glu Pro Pro Glu His Met Ala Glu Leu Gln
1               5                   10                  15
```

<210> SEQ ID NO 8
<211> LENGTH: 29
<212> TYPE: PRT
<213> ORGANISM: Artificial Sequence
<220> FEATURE:
<223> OTHER INFORMATION: Synthetic

<400> SEQUENCE: 8

```
Ala Ala Pro Gly Gln Glu Pro Pro Glu His Met Ala Glu Leu Gln Arg
1               5                   10                  15

Asn Glu Gln Glu Gln Pro Leu Gly Gln Trp His Leu Ser
            20                  25
```

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

```
Asn Glu Gln Glu Gln Pro Leu
1               5
```

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

```
Gly Gln Trp His Leu Ser
1               5
```

<210> SEQ ID NO 11
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature

```
<222> LOCATION: (12)..(12)
<223> OTHER INFORMATION: n is t or u
<220> FEATURE:
<221> NAME/KEY: misc_feature
<222> LOCATION: (17)..(17)
<223> OTHER INFORMATION: n is t or u

<400> SEQUENCE: 11
ancnacangg cngaccngga a                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is t or u
<220> FEATURE:
<221> NAME/KEY: misc_feature
<222> LOCATION: (17)..(18)
<223> OTHER INFORMATION: n is t or u
<220> FEATURE:
<221> NAME/KEY: misc_feature
<222> LOCATION: (20)..(21)
<223> OTHER INFORMATION: n is t or u

<400> SEQUENCE: 12
aggaaagagg gngccgnncn n                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (19)..(21)
<223> OTHER INFORMATION: n is t or u

<400> SEQUENCE: 13
gccaangngg ngagaaagnn n                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (16)..(16)
<223> OTHER INFORMATION: n is t or u
<220> FEATURE:
```

```
<221> NAME/KEY: misc_feature
<222> LOCATION: (20)..(21)
<223> OTHER INFORMATION: n is t or u

<400> SEQUENCE: 14
gccaagaagg ngaacnggan n                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (19)..(21)
<223> OTHER INFORMATION: n is t or u

<400> SEQUENCE: 15
ccggacaang aagaagccnn n                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (17)..(17)
<223> OTHER INFORMATION: n is t or u
<220> FEATURE:
<221> NAME/KEY: misc_feature
<222> LOCATION: (21)..(21)
<223> OTHER INFORMATION: n is t or u

<400> SEQUENCE: 16
ncnagccaca acagggncaa n                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
atctacatgg ctgacctgga a                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
aggaaagagg gtgccgttct t                                              21
```

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
gccaatgtgg tgagaaagtt t                                    21

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
gccaagaagg tgaactggat t                                    21

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ccggacaatg aagaagcctt t                                    21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
tctagccaca acagggtcaa t                                    21

<210> SEQ ID NO 23
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(25)
<223> OTHER INFORMATION: n is any nucleic acid

<400> SEQUENCE: 23
ccggnnnnnn nnnnnnnnnn nnnnnctcga gaaactttct caccacattg gcttttg      58

<210> SEQ ID NO 24
<211> LENGTH: 747
<212> TYPE: PRT
<213> ORGANISM: Homo sapiens

<400> SEQUENCE: 24

Met Arg Arg Cys Asn Ser Gly Ser Gly Pro Pro Pro Ser Leu Leu Leu
1               5                   10                  15

Leu Leu Leu Trp Leu Leu Ala Val Pro Gly Ala Asn Ala Ala Pro Arg
            20                  25                  30

```
Ser Ala Leu Tyr Ser Pro Ser Asp Pro Leu Thr Leu Leu Gln Ala Asp
             35                  40                  45

Thr Val Arg Gly Ala Val Leu Gly Ser Arg Ser Ala Trp Ala Val Glu
 50                  55                  60

Phe Phe Ala Ser Trp Cys Gly His Cys Ile Ala Phe Ala Pro Thr Trp
 65                  70                  75                  80

Lys Ala Leu Ala Glu Asp Val Lys Ala Trp Arg Pro Ala Leu Tyr Leu
                 85                  90                  95

Ala Ala Leu Asp Cys Ala Glu Glu Thr Asn Ser Ala Val Cys Arg Asp
                100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
            130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
            195                 200                 205

Gln His Lys Gly Val Ala Val Arg Arg Val Leu Asn Thr Glu Ala Asn
210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
                260                 265                 270

Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
            290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
            355                 360                 365

Ser Phe Phe Lys Thr Ala Leu Asp Asp Arg Lys Glu Gly Ala Val Leu
            370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
                420                 425                 430

Lys Glu Val Leu Pro Ala Ile Arg Gly Tyr Val His Tyr Phe Phe Gly
            435                 440                 445

Cys Arg Asp Cys Ala Ser His Phe Glu Gln Met Ala Ala Ala Ser Met
```

```
                450             455             460
His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Arg Glu Leu Cys Ser Ala Cys
                500                 505                 510

His Asn Glu Arg Leu Asp Val Pro Val Trp Asp Val Glu Ala Thr Leu
                515                 520                 525

Asn Phe Leu Lys Ala His Phe Ser Pro Ser Asn Ile Ile Leu Asp Phe
530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
                565                 570                 575

Thr Leu Asp Pro Gly Lys Pro Glu Met Met Lys Ser Pro Thr Asn Thr
                580                 585                 590

Thr Pro His Val Pro Ala Glu Gly Pro Glu Ala Ser Arg Pro Pro Lys
                595                 600                 605

Leu His Pro Gly Leu Arg Ala Ala Pro Gly Gln Glu Pro Pro Glu His
                610                 615                 620

Met Ala Glu Leu Gln Arg Asn Glu Gln Glu Gln Pro Leu Gly Gln Trp
625                 630                 635                 640

His Leu Ser Lys Arg Asp Thr Gly Ala Ala Leu Leu Ala Glu Ser Arg
                645                 650                 655

Ala Glu Lys Asn Arg Leu Trp Gly Pro Leu Glu Val Arg Arg Val Gly
                660                 665                 670

Arg Ser Ser Lys Gln Leu Val Asp Ile Pro Glu Gly Gln Leu Glu Ala
                675                 680                 685

Arg Ala Gly Arg Gly Arg Gly Gln Trp Leu Gln Val Leu Gly Gly Gly
                690                 695                 700

Phe Ser Tyr Leu Asp Ile Ser Leu Cys Val Gly Leu Tyr Ser Leu Ser
705                 710                 715                 720

Phe Met Gly Leu Leu Ala Met Tyr Thr Tyr Phe Gln Ala Lys Ile Arg
                725                 730                 735

Ala Leu Lys Gly His Ala Gly His Pro Ala Ala
                740                 745

<210> SEQ ID NO 25
<211> LENGTH: 604
<212> TYPE: PRT
<213> ORGANISM: Homo sapiens

<400> SEQUENCE: 25

Met Arg Arg Cys Asn Ser Gly Ser Gly Pro Pro Pro Ser Leu Leu Leu
1               5                   10                  15

Leu Leu Leu Trp Leu Leu Ala Val Pro Gly Ala Asn Ala Ala Pro Arg
                20                  25                  30

Ser Ala Leu Tyr Ser Pro Ser Asp Pro Leu Thr Leu Leu Gln Ala Asp
                35                  40                  45

Thr Val Arg Gly Ala Val Leu Gly Ser Arg Ser Ala Trp Ala Val Glu
                50                  55                  60

Phe Phe Ala Ser Trp Cys Gly His Cys Ile Ala Phe Ala Pro Thr Trp
65                  70                  75                  80
```

-continued

```
Lys Ala Leu Ala Glu Asp Val Lys Ala Trp Arg Pro Ala Leu Tyr Leu
             85                  90                  95
Ala Ala Leu Asp Cys Ala Glu Glu Thr Asn Ser Ala Val Cys Arg Asp
            100                 105                 110
Phe Asn Ile Pro Gly Phe Pro Thr Val Arg Phe Phe Lys Ala Phe Thr
            115                 120                 125
Lys Asn Gly Ser Gly Ala Val Phe Pro Val Ala Gly Ala Asp Val Gln
            130                 135                 140
Thr Leu Arg Glu Arg Leu Ile Asp Ala Leu Glu Ser His His Asp Thr
145                 150                 155                 160
Trp Pro Pro Ala Cys Pro Pro Leu Glu Pro Ala Lys Leu Glu Glu Ile
                165                 170                 175
Asp Gly Phe Phe Ala Arg Asn Asn Glu Glu Tyr Leu Ala Leu Ile Phe
            180                 185                 190
Glu Lys Gly Gly Ser Tyr Leu Gly Arg Glu Val Ala Leu Asp Leu Ser
            195                 200                 205
Gln His Lys Gly Val Ala Val Arg Arg Val Leu Asn Thr Glu Ala Asn
            210                 215                 220
Val Val Arg Lys Phe Gly Val Thr Asp Phe Pro Ser Cys Tyr Leu Leu
225                 230                 235                 240
Phe Arg Asn Gly Ser Val Ser Arg Val Pro Val Leu Met Glu Ser Arg
                245                 250                 255
Ser Phe Tyr Thr Ala Tyr Leu Gln Arg Leu Ser Gly Leu Thr Arg Glu
            260                 265                 270
Ala Ala Gln Thr Thr Val Ala Pro Thr Thr Ala Asn Lys Ile Ala Pro
            275                 280                 285
Thr Val Trp Lys Leu Ala Asp Arg Ser Lys Ile Tyr Met Ala Asp Leu
            290                 295                 300
Glu Ser Ala Leu His Tyr Ile Leu Arg Ile Glu Val Gly Arg Phe Pro
305                 310                 315                 320
Val Leu Glu Gly Gln Arg Leu Val Ala Leu Lys Lys Phe Val Ala Val
                325                 330                 335
Leu Ala Lys Tyr Phe Pro Gly Arg Pro Leu Val Gln Asn Phe Leu His
            340                 345                 350
Ser Val Asn Glu Trp Leu Lys Arg Gln Lys Arg Asn Lys Ile Pro Tyr
            355                 360                 365
Ser Phe Phe Lys Thr Ala Leu Asp Asp Arg Lys Glu Gly Ala Val Leu
            370                 375                 380
Ala Lys Lys Val Asn Trp Ile Gly Cys Gln Gly Ser Glu Pro His Phe
385                 390                 395                 400
Arg Gly Phe Pro Cys Ser Leu Trp Val Leu Phe His Phe Leu Thr Val
                405                 410                 415
Gln Ala Ala Arg Gln Asn Val Asp His Ser Gln Glu Ala Ala Lys Ala
            420                 425                 430
Lys Glu Val Leu Pro Ala Ile Arg Gly Tyr Val His Tyr Phe Phe Gly
            435                 440                 445
Cys Arg Asp Cys Ala Ser His Phe Glu Gln Met Ala Ala Ala Ser Met
            450                 455                 460
His Arg Val Gly Ser Pro Asn Ala Ala Val Leu Trp Leu Trp Ser Ser
465                 470                 475                 480
His Asn Arg Val Asn Ala Arg Leu Ala Gly Ala Pro Ser Glu Asp Pro
                485                 490                 495
Gln Phe Pro Lys Val Gln Trp Pro Pro Arg Glu Leu Cys Ser Ala Cys
```

```
                500               505               510
His Asn Glu Arg Leu Asp Val Pro Val Trp Asp Val Glu Ala Thr Leu
        515               520               525

Asn Phe Leu Lys Ala His Phe Ser Pro Ser Asn Ile Ile Leu Asp Phe
    530               535               540

Pro Ala Ala Gly Ser Ala Arg Arg Asp Val Gln Asn Val Ala Ala
545               550               555               560

Ala Pro Glu Leu Ala Met Gly Ala Leu Glu Leu Glu Ser Arg Asn Ser
            565               570               575

Thr Leu Asp Pro Gly Lys Pro Glu Met Met Lys Ser Pro Thr Asn Thr
        580               585               590

Thr Pro His Val Pro Ala Glu Gly Pro Glu Leu Ile
        595               600
```

<210> SEQ ID NO 26
<211> LENGTH: 58
<212> TYPE: DNA
<213> ORGANISM: Artificial Sequence
<220> FEATURE:
<223> OTHER INFORMATION: Synthetic

<400> SEQUENCE: 26
ccgggccaat gtggtgagaa agtttctcga gaaactttct caccacattg gcttttg    58

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
ccggacaatg aagaagccct t                                            21

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
tctagccaca acagggtcaa t                                            21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
tccgtggtgg acagccacat g                                            21

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
ggcctccaag gagtaagacc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
aggggtctac atggcaactg                                              20

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
tggtctagcc acaacagggt caat                                         24

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
tgtggcaggc agaacaaagt tcac                                         24

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
ttgctccttg tctggcctag aagt                                         24

<210> SEQ ID NO 35
<211> LENGTH: 26
<212> TYPE: DNA
<213> ORGANISM: Artificial Sequence
<220> FEATURE:
<223> OTHER INFORMATION: Synthetic

<400> SEQUENCE: 35
tgtgtcaaag gagctctctc tgtcct                                       26

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
ttgacggtaa ggacggactc                                              20

<210> SEQ ID NO 37
<211> LENGTH: 20
<212> TYPE: DNA
<213> ORGANISM: Artificial Sequence
<220> FEATURE:

```
<223> OTHER INFORMATION: Synthetic

<400> SEQUENCE: 37
acttgcagta ctccccatcg                                           20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
ttgacagcga caagaagtgg                                           20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ccctcagtga agcggtacat                                           20

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
atctacatgg ctgacctgga a                                         21

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
aggaaagagg gtgccgttct t                                         21
```